United States Patent
Zambach et al.

(10) Patent No.: US 10,357,035 B2
(45) Date of Patent: Jul. 23, 2019

(54) MICROBIOCIDAL ANILIDE DERIVATIVES

(71) Applicant: SYNGENTA PARTICIPATIONS AG, Basel (CH)

(72) Inventors: Werner Zambach, Stein (CH); Clemens Lamberth, Stein (CH); Martin Pouliot, Stein (CH); Stefano Rendine, Stein (CH); Mathias Blum, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/773,467

(22) PCT Filed: Nov. 3, 2016

(86) PCT No.: PCT/EP2016/076579
§ 371 (c)(1),
(2) Date: May 3, 2018

(87) PCT Pub. No.: WO2017/076982
PCT Pub. Date: May 11, 2017

(65) Prior Publication Data
US 2018/0317482 A1 Nov. 8, 2018

(30) Foreign Application Priority Data
Nov. 4, 2015 (EP) .................... 15193046

(51) Int. Cl.
*C07D 263/56* (2006.01)
*A01N 43/40* (2006.01)
*C07D 213/69* (2006.01)
*C07D 213/81* (2006.01)

(52) U.S. Cl.
CPC .......... *A01N 43/40* (2013.01); *C07D 213/69* (2013.01); *C07D 213/81* (2013.01); *C07D 263/56* (2013.01)

(58) Field of Classification Search
None
See application file for complete search history.

(56) References Cited

U.S. PATENT DOCUMENTS 6,521,622 B1 * 2/2003 Ricks ..................... A01N 43/40
514/252.01

FOREIGN PATENT DOCUMENTS

| WO | 2001/05769 A2 | 1/2001 |
| WO | 2001/14339 A2 | 3/2001 |

OTHER PUBLICATIONS

International Search Report and Written Opinion for PC/EP2016/076579, dated Jan. 30, 2017, 10 pages.

* cited by examiner

*Primary Examiner* — Bong-Sook Baek
(74) *Attorney, Agent, or Firm* — Baker & Hostetler LLP; Toni-Junell Herbert

(57) ABSTRACT

Compounds of the formula (I) wherein the substituents are as defined in claim 1, useful as a pesticides, and especially fungicides.

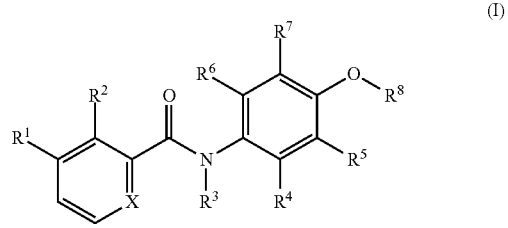

(I)

12 Claims, No Drawings

MICROBIOCIDAL ANILIDE DERIVATIVES

CROSS-REFERENCE TO RELATED APPLICATIONS

This application is a 371 National Stage application of International Application No. PCT/EP2016/076579, filed Nov. 3, 2016, which claims priority to European Patent Application No. 15193046.8, filed Nov. 4, 2015, the entire contents of which are hereby incorporated by reference.

The present invention relates to microbiocidal anilide derivatives, e.g., as active ingredients, which have microbiocidal activity, in particular fungicidal activity. The invention also relates to the preparation of these anilide derivatives, to agrochemical compositions which comprise at least one of the anilide derivatives and to uses of the anilide derivatives or compositions thereof in agriculture or horticulture for controlling or preventing the infestation of plants, harvested food crops, seeds or non-living materials by phytopathogenic microorganisms, preferably fungi.

WO 01/14339 and WO 01/05769 disclose fungicidally-active heterocyclic aromatic amide compounds.

According to the present invention, there is provided a compound of formula (I):

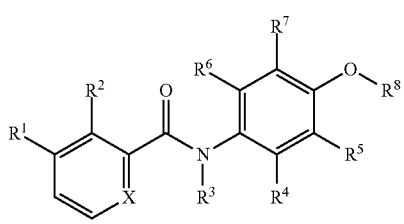

(I)

wherein, $R^1$ is $C_1$-$C_6$alkoxy or $C_1$-$C_6$acylamino, wherein $C_1$-$C_6$alkoxy and $C_1$-$C_6$acylamino are optionally substituted with 1 to 3 groups represented by $R^9$; and $R^2$ is hydroxyl, $C_1$-$C_6$acyloxy, $C_1$-$C_6$alkoxy$C_1$-$C_6$alkoxy or $C_1$-$C_6$acyloxy$C_1$-$C_6$alkoxy, wherein $C_1$-$C_6$acyloxy, $C_1$-$C_6$alkoxy$C_1$-$C_6$alkoxy and $C_1$-$C_6$acyloxy$C_1$-$C_6$alkoxy are optionally substituted with 1 to 3 groups represented by $R^9$; or $R^1$ and $R^2$ together with the carbon atoms to which they are attached form a 1,3-oxazole ring;

$R^3$ is hydrogen, $C_1$-$C_6$alkyl, $C_1$-$C_6$alkoxy or $C_3$-$C_6$cycloalkyl;

$R^4$, $R^5$, $R^6$ and $R^7$ are independently hydrogen, halogen, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^9$;

$R^8$ is $C_3$-$C_9$cycloalkyl optionally substituted with 1 to 5 groups represented by $R^{10}$, wherein $R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy, wherein $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy are optionally substituted with 1 to 3 groups represented by $R^9$; or $R^8$ is $C_3$-$C_9$cycloalkyl optionally substituted with 1 or 2 groups represented by $R^{10}$, wherein $R^{10}$ is independently selected from $C_3$-$C_6$cycloalkyl, aryl, heteroaryl, aryloxy, heteroaryloxy, aryl$C_1$-$C_6$alkyl, heteroaryl$C_1$-$C_6$alkyl, =O, =C($R^{11}$)$_2$, =NOR$^{11}$ or =N—N($R^{11}$)$_2$, wherein $C_3$-$C_6$cycloalkyl, aryl, heteroaryl, aryloxy, heteroaryloxy, aryl$C_1$-$C_6$alkyl or heteroaryl$C_1$-$C_6$alkyl are optionally substituted with 1 to 3 groups represented by $R^9$; or $R^8$ is $C_3$-$C_9$cycloalkyl optionally substituted with 1 group represented by $R^{10}$, wherein $R^{10}$ is a spiro-annulated 3- to 10-membered saturated or partially unsaturated carbocyclic ring system or heterocyclic ring system containing 1 to 3 heteroatoms selected from oxygen, nitrogen and sulfur, and optionally substituted by 1 to 5 groups represented by halogen, $C_1$-$C_4$alkyl or =O;

$R^9$ is independently selected from halogen, cyano, $C_1$-$C_4$alkyl and $C_1$-$C_4$alkoxy, wherein $C_1$-$C_4$alkyl and $C_1$-$C_4$alkoxy are optionally substituted by 1 to 5 groups represented by halogen;

$R^{11}$ is hydrogen, $C_1$-$C_6$alkyl, $C_2$-$C_6$alkenyl, $C_2$-$C_6$alkynyl or aryl, wherein $C_1$-$C_6$alkyl, $C_2$-$C_6$alkenyl, $C_2$-$C_6$alkynyl and aryl are optionally substituted with 1 to 3 groups represented by $R^9$; and X is CH or N;

or a salt or an N-oxide thereof;

with the proviso that the compound of formula (I) is not 3-hydroxy-4-methoxy-N-[4-(3,3,5,5-tetramethylcyclohexoxy)phenyl]pyridine-2-carboxamide.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I) according to the present invention.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may exclude methods for the treatment of the human or animal body by surgery or therapy.

Where substituents are indicated as being "optionally substituted", this means that they may or may not carry one or more identical or different substituents, e.g., one, two or three $R^9$ substituents. For example, $C_1$-$C_6$alkyl substituted by 1, 2 or 3 halogens, may include, but not be limited to, —CH$_2$Cl, —CHCl$_2$, —CCl$_3$, —CH$_2$F, —CHF$_2$, —CF$_3$, —CH$_2$CF$_3$ or —CF$_2$CH$_3$ groups. As another example, $C_1$-$C_6$alkoxy substituted by 1, 2 or 3 halogens, may include, but not be limited to, CH$_2$ClO—, CHCl$_2$O—, CCl$_3$O—, CH$_2$FO—, CHF$_2$O—, CF$_3$O—, CF$_3$CH$_2$O— or CH$_3$CF$_2$O— groups.

As used herein, the term "hydroxyl" or "hydroxy" stands for a —OH group.

As used herein, the term "cyano" means a —CN group.

As used herein, the term "halogen" refers to fluorine, chlorine, bromine or iodine.

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_4$alkyl" is to be construed accordingly. Examples of $C_1$-$C_6$alkyl include, but are not limited to, methyl, ethyl, n-propyl, n-butyl, n-pentyl, n-hexyl and the isomers thereof, for example, iso-propyl, iso-butyl, sec-butyl, tert-butyl or iso-amyl. A "$C_1$-$C_6$alkylene" group refers to the corresponding definition of $C_1$-$C_6$alkyl, except that such radical is attached to the rest of the molecule by two single bonds. Examples of $C_1$-$C_6$alkylene, include, but are not limited to, —$CH_2$—, —$CH_2CH_2$— and —$(CH_2)_3$—.

As used herein, the term "$C_2$-$C_6$ alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. The term "$C_2$-$C_4$alkenyl" and "$C_2$-$C_3$alkenyl" are to be construed accordingly. Examples of $C_2$-$C_6$alkenyl include, but are not limited to, ethenyl (vinyl), prop-1-enyl, prop-2-enyl (allyl), but-1-enyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_4$ alkynyl" and "$C_2$-$C_3$ alkynyl" are to be construed accordingly. Examples of $C_2$-$C_6$alkynyl include, but are not limited to, ethynyl, prop-1-ynyl, but-1-ynyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_4$alkoxy" is to be construed accordingly. Examples of $C_1$-$C_6$ alkoxy include, but are not limited to, methoxy, ethoxy, 1-methylethoxy (iso-propoxy), propoxy, butoxy, 1-methylpropoxy and 2-methylpropoxy.

As used herein, the term "$C_3$-$C_9$cycloalkyl" refers to a radical which is a mono- or bicyclic saturated ring system and which contains 3 to 9 carbon atoms, which may include an alkylene-bridged ring system. $C_3$-$C_6$cycloalkyl and $C_3$-$C_5$cycloalkyl are to be construed accordingly. Examples of $C_3$-$C_9$cycloalkyl include, but are not limited to, cyclopropyl, 1-methylcyclopropyl, 2-methylcyclopropyl, cyclobutyl, cyclopentyl and cyclohexyl, cycloheptyl, cyclooctyl or norbornyl.

As used herein, the term "heterocyclyl" or "heterocyclic" refers to a stable 5- or 6-membered non-aromatic monocyclic ring which comprises 1, 2 or 3 heteroatoms, or a 9- or 10-membered bicyclic ring which comprises 1, 2, 3, 4 or 5 heteroatoms (including 1, 2, or 3 heteroatoms), wherein the heteroatoms are individually selected from nitrogen, oxygen and sulfur. The heterocyclyl radical may be bonded to the rest of the molecule via a carbon atom or heteroatom. Examples of heterocyclyl include, but are not limited to, aziridinyl, azetidinyl, oxetanyl, thietanyl, tetrahydrofuryl, pyrrolidinyl, pyrazolidinyl, imidazolidnyl, piperidinyl, piperazinyl, morpholinyl, dioxolanyl, dithiolanyl and thiazolidinyl.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "aryl$C_1$-$C_6$alkyl" refers to an aryl ring attached to the rest of the molecule by a $C_1$-$C_6$alkyl radical as defined above. Examples of aryl$C_1$-$C_6$alkyl include, but are not limited to benzyl or 2-phenylethyl.

As used herein, the term "heteroaryl" refers to a 5- or 6-membered aromatic monocyclic ring radical which comprises 1, 2, 3 or 4 heteroatoms individually selected from nitrogen, oxygen and sulfur. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_1$-$C_6$alkyl" refers to a heteroaryl ring attached to the rest of the molecule by a $C_1$-$C_6$ alkyl radical as defined above.

As used herein, the term "aryloxy" refers to a radical of the formula —$OR_a$ where $R_a$ is an aryl radical as generally defined above. Aryloxy groups include, but are not limited to, phenoxy.

As used herein, the term "heteroaryloxy" refers to a radical of the formula —$OR_a$ where $R_a$ is a heteroaryl radical as generally defined above.

As used herein, the term "$C_2$-$C_6$acyl" refers to a radical $R_aC(=O)$—, where $R_a$ is $C_1$-$C_6$alkyl radical or aryl radical as generally defined above. Acyl groups include, but are not limited to, acetyl, propanoyl and benzoyl.

As used herein, the term "$C_1$-$C_6$acyloxy" refers to a radical of the formula —$OR_b$ where $R_b$ is a formyl or a $C_2$-$C_6$acyl radical as generally defined above. $C_1$-$C_6$acyloxy groups include, but are not limited to, acetoxy.

As used herein, the term "$C_1$-$C_6$acylamino" refers to a radical of the formula —$NHR_c$, where $R_c$ is a formyl or a $C_2$-$C_6$acyl radical as generally defined above.

As used herein, the term "$C_1$-$C_6$alkoxy-$C_1$-$C_6$alkoxy" refers to a radical —$OR_a$—$OR_b$, wherein $R_a$ is a $C_1$-$C_6$ alkylene group as generally defined above and $R_b$, is a $C_1$-$C_6$ alkyl group as generally defined above.

As used herein, the term "$C_1$-$C_6$acyloxy-$C_1$-$C_6$alkoxy" refers to a radical —$OR_a$—$OC(=O)$—$R_b$, wherein $R_a$ is a $C_1$-$C_6$alkylene group and $R_b$ is a $C_1$-$C_6$alkyl group as generally defined above.

As used herein, the term $C_1$-$C_6$alkylthio means an —$SR_a$ group, wherein $R_a$ is a $C_1$-$C_6$alkyl radical as generally defined above.

As used herein, the term "oxazole" means 1,3-oxazole.

As used herein, the term $C_1$-$C_6$ alkylsulfonyl means an —$S(O)_2R_a$ group, wherein $R_a$ is a $C_1$-$C_6$alkyl radical as generally defined above.

As used herein, the term $C_1$-$C_6$alkylcarbonyloxy means an —$OC(=O)R_a$ group, wherein $R_a$ is a $C_1$-$C_6$alkyl radical as generally defined above.

As used herein, =O means an oxo group, e.g., as found in a carbonyl (—$C(=O)$—) group.

As used herein, the term "spiro-annulated" with reference to the optional substitution of $R^8$ by $R^{10}$ means that the substitution results in the formation of a spirocyclic moiety (consisting of 2 or 3 rings) and the number of ring members (i.e., 3- to 10-membered, 3- to 6-membered, etc) contributed to the spirocyclic moiety by $R^{10}$ is counted including the spirocyclic carbon shared with $R^8$.

The presence of one or more possible asymmetric carbon atoms in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I).

Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents $R^1, R^2, R^3, R^4, R^5, R^6, R^7, R^8, R^9, R^{10}, R^{11}$ and X with reference to compounds of formula (I). For any one of these substituents, any of the definitions given below may be combined with any definition of any other substituent given below or elsewhere in this document.

$R^1$ is $C_1$-$C_6$alkoxy or $C_1$-$C_6$acylamino, wherein $C_1$-$C_6$alkoxy and $C_1$-$C_6$acylamino are optionally substituted with 1 to 3 groups represented by $R^9$. Preferably, $R^1$ is $C_1$-$C_6$alkoxy, more preferably $C_1$-$C_4$alkoxy, even more preferably methoxy, ethoxy or iso-propoxy, and most preferably methoxy.

$R^2$ is hydroxyl, $C_1$-$C_6$acyloxy, $C_1$-$C_6$alkoxy$C_1$-$C_6$alkoxy or $C_1$-$C_6$acyloxy$C_1$-$C_6$alkoxy, wherein $C_1$-$C_6$acyloxy, $C_1$-$C_6$alkoxy$C_1$-$C_6$alkoxy and $C_1$-$C_6$acyloxy$C_1$-$C_6$alkoxy are optionally substituted with 1 to 3 groups represented by $R^9$. Preferably, $R^2$ is hydroxyl, $C_1$-$C_4$acyloxy or $C_1$-$C_4$acyloxy$C_1$-$C_4$alkoxy, and more preferably hydroxyl, acetoxy or isobutyryloxymethoxy.

In some embodiments of the invention, $R^1$ is $C_1$-$C_4$alkoxy and $R^2$ is hydroxyl.

In other embodiments of the invention, $R^1$ and $R^2$ together with the carbon atoms to which they are attached form an oxazole ring.

$R^3$ is hydrogen, $C_1$-$C_6$alkyl, $C_1$-$C_6$alkoxy or $C_3$-$C_6$cycloalkyl. Preferably $R^3$ is hydrogen, methyl or methoxy, and more preferably hydrogen.

$R^4, R^5, R^6$ and $R^7$ are independently hydrogen, halogen, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^9$. Preferably, $R^4, R^5, R^6$ and $R^7$ are independently hydrogen or halogen; or $R^4$ is halogen (e.g., fluorine or chlorine) and $R^5, R^6$ and $R^7$ are hydrogen.

In some embodiments of the invention $R^4$ is halogen, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^9$. Preferably, $R^4$ is hydrogen, fluorine or chlorine, and $R^5, R^6$ and $R^7$ are hydrogen.

$R^8$ is $C_3$-$C_9$cycloalkyl optionally substituted with 1 to 5 groups represented by $R^{10}$, wherein $R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy, wherein $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy are optionally substituted with 1 to 3 groups represented by $R^9$; or $C_3$-$C_9$cycloalkyl optionally substituted with 1 or 2 groups represented by $R^{10}$, wherein $R^{19}$ is independently selected from $C_3$-$C_6$cycloalkyl, aryl, heteroaryl, aryloxy, heteroaryloxy, aryl$C_1$-$C_6$alkyl, heteroaryl$C_1$-$C_6$alkyl, =O, =C($R^{11}$)$_2$, =NOR$^{11}$ or =N—N($R^{11}$)$_2$, wherein $C_3$-$C_6$cycloalkyl, aryl, heteroaryl, aryloxy, heteroaryloxy, aryl$C_1$-$C_6$alkyl or heteroaryl$C_1$-$C_6$alkyl are optionally substituted with 1 to 3 groups represented by $R^9$; or $C_3$-$C_9$cycloalkyl is optionally substituted with 1 group represented by $R^{10}$, wherein $R^{10}$ is a spiro-annulated 3- to 10-membered saturated or partially unsaturated carbocyclic ring system or heterocyclic ring system containing 1 to 3 heteroatoms selected from oxygen, nitrogen and sulfur, optionally substituted by 1 to 5 groups represented by halogen, $C_1$-$C_4$alkyl or =O.

In certain embodiments of the invention, $R^8$ is $C_3$-$C_9$cycloalkyl optionally substituted with 1 group represented by $R^{10}$, wherein $R^{10}$ is a spiro-annulated 3- to 6-membered saturated or partially unsaturated carbocyclic ring system or heterocyclic ring system containing 1 to 3 heteroatoms selected from oxygen, nitrogen and sulfur, optionally substituted by 1 to 5 groups represented by halogen, $C_1$-$C_4$alkyl or =O.

Alternatively, $R^8$ is $C_3$-$C_6$cycloalkyl optionally substituted with 1 group represented by $R^{10}$, wherein $R^{10}$ is a spiro-annulated 3- to 6-membered (or 3- to 5-membered) saturated or partially unsaturated carbocyclic ring system or heterocyclic ring system containing 1 or 2 heteroatoms selected from oxygen, nitrogen and sulfur, optionally substituted by 1 to 3 groups represented by halogen, $C_1$-$C_4$alkyl or =O.

Preferably, $R^8$ is $C_3$-$C_9$cycloalkyl optionally substituted with 1 to 3 groups represented by $R^{10}$, wherein $R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy; or $C_3$-$C_9$cycloalkyl optionally substituted with 1 or 2 groups represented by $R^{10}$, wherein $R^{10}$ is independently selected from $C_3$-$C_6$cycloalkyl, aryl, heteroaryl, aryloxy, heteroaryloxy, aryl$C_1$-$C_6$alkyl, heteroaryl$C_1$-$C_6$alkyl, =O, =C($R^{11}$)$_2$, =NOR$^{11}$ or =N—N($R^{11}$)$_2$, wherein $C_3$-$C_6$cycloalkyl, aryl, heteroaryl, aryloxy, heteroaryloxy, aryl$C_1$-$C_6$alkyl or heteroaryl$C_1$-$C_6$alkyl are optionally substituted with 1 to 3 groups represented by $R^9$; or $C_3$-$C_9$cycloalkyl optionally substituted with 1 group represented by $R^{10}$, wherein $R^{10}$ is a spiro-annulated 3- to 10-membered (or 3- to 6-membered) saturated or partially unsaturated carbocyclic ring system or heterocyclic ring system containing 1 or 2 heteroatoms selected from oxygen, nitrogen and sulfur, optionally substituted by 1 to 3 groups represented by halogen, $C_1$-$C_4$alkyl or =O.

More preferably, $R^8$ is $C_7$-$C_9$cycloalkyl optionally substituted with 1 to 5 groups represented by $R^{10}$, wherein $R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy, wherein $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy are optionally substituted with 1 to 3 groups represented by $R^9$; or $C_3$-$C_9$cycloalkyl optionally substituted with 1 or 2 groups represented by $R^{10}$, wherein $R^{10}$ is independently selected from $C_3$-$C_6$cycloalkyl, aryl, heteroaryl, aryloxy, heteroaryloxy, aryl$C_1$-$C_6$alkyl, heteroaryl$C_1$-$C_6$alkyl, =O, =C($R^{11}$)$_2$, =NOR$^{11}$ or =N—N($R^{11}$)$_2$, wherein $C_3$-$C_6$cycloalkyl, aryl, heteroaryl, aryloxy, heteroaryloxy, aryl$C_1$-$C_6$alkyl or heteroaryl$C_1$-$C_6$alkyl are optionally substituted with 1 to 3 groups represented by $R^9$; or $C_3$-$C_9$cycloalkyl is optionally substituted with 1 group represented by $R^{10}$, wherein $R^{10}$ is a spiro-annulated 3- to 10-membered (or 3- to 6-membered) saturated or partially unsaturated carbocyclic ring system or heterocyclic ring system containing 1 or 2 heteroatoms selected from oxygen, nitrogen and sulfur, optionally substituted by 1 to 3 groups represented by halogen, $C_1$-$C_4$alkyl or =O.

Even more preferably, $R^8$ is $C_5$-$C_8$cycloalkyl optionally substituted with 1 or 2 groups represented by $R^{10}$, wherein $R^{10}$ is independently selected from hydroxyl, $C_1$-$C_6$alkyl, $C_1$-$C_6$alkylcarbonyloxy, $C_3$-$C_6$cycloalkyl, aryl, =$C(R^{11})_2$, =$NOR^{11}$; or $R^8$ is $C_5$-$C_8$cycloalkyl optionally substituted with 1 group represented by $R^{10}$ which is spiro-annulated 1,3-dioxolan-2-yl, wherein $C_1$-$C_6$alkyl, $C_3$-$C_6$cycloalkyl, aryl, =$C(R^{11})_2$ and =$NOR^{11}$ are optionally substituted with 1 to 3 groups represented by $R^9$, or spiro-annulated 1,3-dioxolan-2-yl is optionally substituted by 1 to 3 groups represented by halogen, $C_1$-$C_4$alkyl or =O; and $R^{11}$ is independently selected from hydrogen, $C_1$-$C_6$alkyl, $C_2$-$C_6$alkenyl, $C_2$-$C_6$alkynyl and aryl.

Still more preferably, $R^8$ is $C_5$-$C_8$cycloalkyl optionally substituted with 1 or 2 groups represented by $R^{10}$, wherein $R^{10}$ is independently selected from hydroxyl, $C_1$-$C_4$alkyl, $C_1$-$C_6$alkylcarbonyloxy, $C_6$cycloalkyl, phenyl, =$C(R^{11})_2$ or =$NOR^{11}$, and $R^{11}$ is independently selected from hydrogen, $C_1$-$C_4$alkyl, $C_2$-$C_4$alkenyl, $C_2$-$C_4$alkynyl and phenyl.

In some embodiments of the invention, in compounds of Formula (I) when $R^8$ is cyclohexyl, only one carbon ring atom (positions 2- to 6-) may be substituted by two groups represented by $R^9$ which is methyl. In other embodiments of the invention, in compounds of Formula (I) when $R^8$ is cyclohexyl substituted by four groups represented by $R^9$ which are methyl and wherein $R^9$ consists of two dimethyl moieties, at least one of the 2- or 4-positions of cyclohexyl is dimethyl-substituted.

In a further embodiment of the invention, in compounds of Formula (I), when $R^8$ is cyclohexyl substituted by four groups represented by $R^9$ which are methyl and, wherein two cyclohexyl ring carbon positions are each substituted by two methyl groups, at least one of $R^3$, $R^4$, $R^5$, $R^6$, and $R^7$ is not hydrogen.

$R^9$ is independently selected from halogen, cyano, $C_1$-$C_4$alkyl and $C_1$-$C_4$alkoxy, wherein $C_1$-$C_4$alkyl and $C_1$-$C_4$alkoxy are optionally substituted by 1 to 5 groups represented by halogen. Preferably, $R^9$ is chloro, fluoro, cyano, methyl, methoxy or ethoxy. Preferably, each substituted $R^1$, $R^2$, $R^4$, $R^5$, $R^6$, $R^7$ or $R^{10}$ group has one or two $R^9$ substituent(s), and more preferably, one $R^9$ substituent.

$R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_3$-$C_6$cycloalkyl, $C_2$-$C_6$alkenyl, $C_2$-$C_6$alkynyl, $C_1$-$C_6$alkylcarbonyloxy, aryl, heteroaryl, aryloxy, heteroaryloxy, aryl$C_1$-$C_6$alkyl, heteroaryl$C_1$-$C_6$alkyl, =O, =$C(R^{11})_2$, =$NOR^{11}$ or =N—$N(R^{11})_2$, wherein $C_1$-$C_6$alkyl, $C_1$-$C_6$alkoxy, $C_1$-$C_6$alkylthio, $C_1$-$C_6$alkylsulfonyl, $C_3$-$C_6$cycloalkyl, aryl, heteroaryl, aryloxy, heteroaryloxy, aryl$C_1$-$C_6$alkyl and heteroaryl$C_1$-$C_6$alkyl are optionally substituted with 1 to 3 groups represented by $R^9$. Preferably, $R^{10}$ is $C_1$-$C_6$alkyl, $C_3$-$C_6$cycloalkyl, aryl, =$C(R^{11})_2$, =$NOR^{11}$ or spiro-annulated 1,3-dioxolan-2-yl optionally substituted with 1 to 3 groups represented by $R^9$, or wherein spiro-annulated 1,3-dioxolan-2-yl is optionally substituted by 1 to 3 groups represented by halogen, $C_1$-$C_4$alkyl or =O, wherein $R^{11}$ is independently selected from hydrogen, $C_1$-$C_6$alkyl, $C_2$-$C_6$alkenyl, $C_2$-$C_6$alkynyl and aryl. More preferably, $R^{10}$ is $C_1$-$C_4$alkyl, $C_6$cycloalkyl, phenyl, =$C(R^{11})_2$ or =$NOR^{11}$, wherein $R^{11}$ is independently selected from hydrogen, $C_1$-$C_4$alkyl, $C_2$-$C_4$alkenyl, $C_2$-$C_4$alkynyl and phenyl.

In some embodiments of the invention, $R^{10}$ is a spiro-annulated 3- to 10-membered saturated or partially unsaturated carbocyclic ring system or heterocyclic ring system containing 1 to 3 heteroatoms selected from oxygen, nitrogen and sulfur, optionally substituted by halogen, $C_1$-$C_4$alkyl or =O.

$R^{11}$ is hydrogen, $C_1$-$C_6$alkyl, $C_2$-$C_6$alkenyl, $C_2$-$C_6$alkynyl or aryl, wherein $C_1$-$C_6$alkyl, $C_2$-$C_6$alkenyl, $C_2$-$C_6$alkynyl and aryl are optionally substituted with 1 to 3 groups represented by $R^9$. Preferably $R^{11}$ is hydrogen, $C_1$-$C_6$alkyl or aryl. Even more preferably $R^{11}$ is hydrogen or $C_1$-$C_6$alkyl.

X is CH or N. Preferably, X is N.

In accordance with the present invention, $R^1$, $R^2$, $R^4$, $R^5$, $R^6$, $R^7$, may optionally be substituted by 1, 2 or 3 $R^9$ substituents. $R^8$ may be optionally substituted by 1, 2, 3, 4 or 5 $R^{10}$ substituents, in particular by 1 or 2 $R^{10}$ substituents.

In accordance with the present invention, the compounds of Formula (I) may be as follows, wherein:

Preferably, $R^1$ is $C_1$-$C_6$alkoxy optionally substituted with 1 to 3 groups represented by $R^9$;
$R^2$ is hydroxyl, $C_1$-$C_6$acyloxy or $C_1$-$C_6$acyloxy$C_1$-$C_6$alkoxy, wherein $C_1$-$C_6$acyloxy and $C_1$-$C_6$acyloxy$C_1$-$C_6$alkoxy are optionally substituted with 1 to 3 groups represented by $R^9$; or
$R^1$ and $R^2$ together with the carbon atoms to which they are attached form a 1,3-oxazole ring;
$R^3$ is hydrogen, methyl or methoxy;
$R^4$, $R^5$, $R^6$ and $R^7$ are independently hydrogen or halogen;
$R^8$ is $C_5$-$C_8$cycloalkyl optionally substituted with 1 to 2 groups represented by $R^{10}$;
$R^9$ is independently selected from hydroxyl, chloro, fluoro, methyl, methoxy or ethoxy;
$R^{10}$ is independently selected from $C_1$-$C_6$alkyl, $C_1$-$C_6$alkoxy, $C_3$-$C_6$cycloalkyl, aryl, aryloxy, aryl$C_1$-$C_6$alkyl, =$C(R^{11})_2$, =$NOR^{11}$ and =O;
$R^{11}$ is independently selected from hydrogen, $C_1$-$C_6$alkyl, $C_2$-$C_6$alkenyl, $C_2$-$C_6$alkynyl and aryl; and
X is CH or N.

More preferably, $R^1$ is $C_1$-$C_4$alkoxy;
$R^2$ is hydroxyl, $C_1$-$C_4$acyloxy or $C_1$-$C_4$acyloxy$C_1$-$C_4$alkoxy;
$R^3$ is hydrogen, methyl or methoxy;
$R^4$ is hydrogen or halogen;
$R^5$, $R^6$ and $R^7$ are independently hydrogen or halogen;
$R^8$ is $C_5$-$C_8$cycloalkyl optionally substituted with 1 or 2 groups represented by $R^{10}$;
$R^{10}$ is independently selected from $C_1$-$C_4$alkyl, $C_3$-$C_6$cycloalkyl, aryl, =$C(R^{11})_2$ and =$NOR^{11}$;
$R^{11}$ is independently selected from hydrogen, $C_1$-$C_6$alkyl, $C_2$-$C_6$alkenyl, $C_2$-$C_6$alkynyl and aryl; and
X is N.

Even more preferably, $R^1$ is methoxy;
$R^2$ is hydroxyl or $C_1$-$C_4$acyloxy$C_1$-$C_4$alkoxy;
$R^3$ is hydrogen;
$R^4$ is hydrogen or fluorine;
$R^5$, $R^6$ and $R^7$ are hydrogen;
$R^8$ is cyclohexyl, cycloheptyl or cyclooctyl optionally substituted by 1 or 2 groups represented by $R^{10}$;
$R^{10}$ is $C_1$-$C_4$alkyl or aryl; and
X is N.

Preferably, the compound according to Formula (I) is selected from:

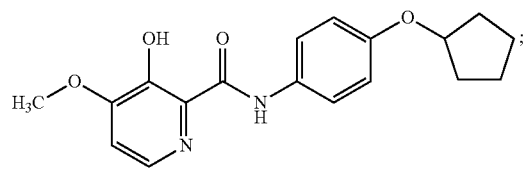

N-[4-(cyclopentoxy)phenyl]-3-hydroxy-4-methoxy-pyridine-2-carboxamide

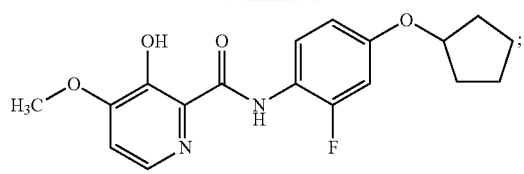

N-[4-(cyclopentoxy)-2-fluoro-phenyl]-3-hydroxy-4-methoxy-pyridine-2-carboxamide

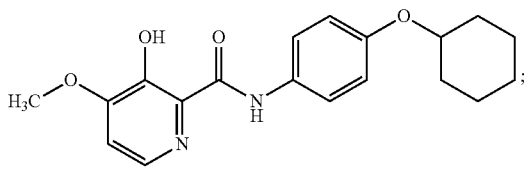

N-[4-(cyclohexoxy)phenyl]-3-hydroxy-4-methoxy-pyridine-2-carboxamide

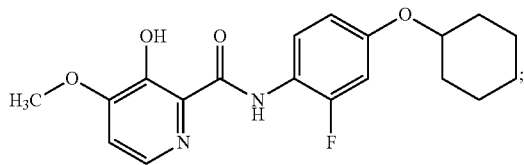

N-[4-(cyclohexoxy)-2-fluoro-phenyl]-3-hydroxy-4-methoxy-pyridine-2-carboxamide

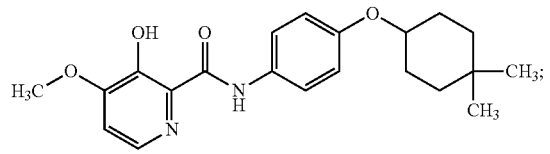

N-[4-(4,4-dimethylcyclohexoxy)phenyl]-3-hydroxy-4-methoxy-pyridine-2-carboxamide

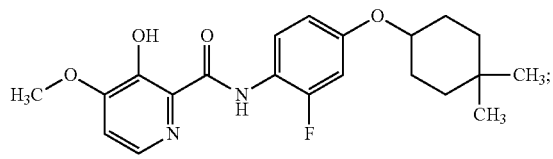

N-[4-(4,4-dimethylcyclohexoxy)-2-fluoro-phenyl]-3-hydroxy-4-methoxy-pyridine-2-carboxamide

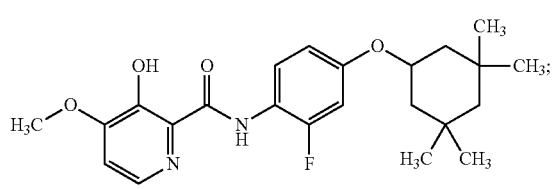

N-[2-fluoro-4-(3,3,5,5-tetramethylcyclohexoxy)phenyl]-3-hydroxy-4-methoxy-pyridine-2-carboxamide

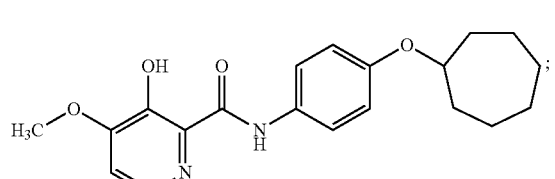

N-[4-(cycloheptoxy)phenyl]-3-hydroxy-4-methoxy-pyridine-2-carboxamide

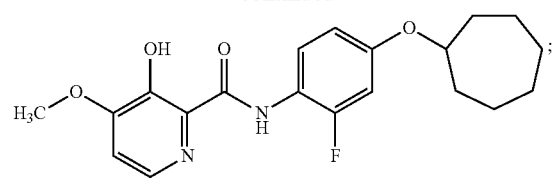

N-[4-(cycloheptoxy)-2-fluoro-phenyl]-3-hydroxy-4-methoxy-pyridine-2-carboxamide

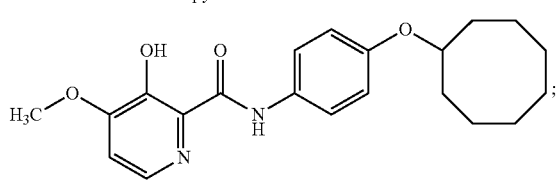

N-[4-(cyclooctoxy)phenyl]-3-hydroxy-4-methoxy-pyridine-2-carboxamide

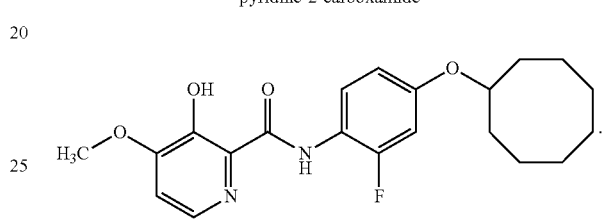

N-[4-(cyclooctoxy)-2-fluoro-phenyl]-3-hydroxy-4-methoxy-pyridine-2-carboxamide

The invention also relates to compounds of formula I-1:

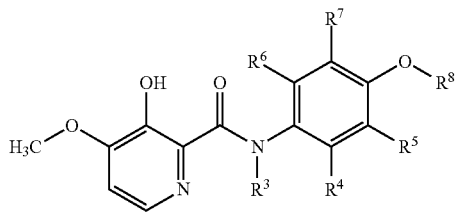

(I-1)

in which $R^3$, $R^4$, $R^5$, $R^6$, $R^7$ and $R^8$ have the definitions as described for formula I. Preferred definitions of $R^3$, $R^4$, $R^5$, $R^6$, $R^7$ and $R^8$ are as defined for formula (I).

The invention also relates to compounds of formula I-2:

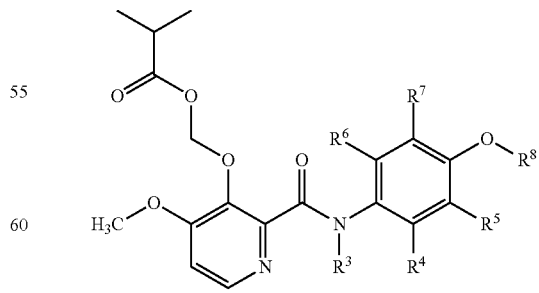

(I-2)

wherein $R^3$, $R^4$, $R^5$, $R^6$, $R^7$ and $R^8$ have the definition as described for formula I. Preferred definitions of $R^3$, $R^4$, $R^5$, $R^6$, $R^7$ and $R^8$ are as defined for formula (I).

The invention also relates to compounds of formula I-3:

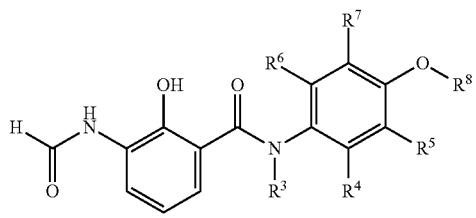

(I-3)

wherein $R^3$, $R^4$, $R^5$, $R^6$, $R^7$ and $R^8$ have the definition as described for formula (I). Preferred definitions of $R^3$, $R^4$, $R^5$, $R^6$, $R^7$ and $R^8$ are as defined for formula (I).

The invention also relates to compounds of formula I-4:

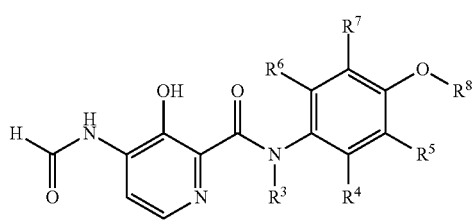

(I-4)

wherein $R^3$, $R^4$, $R^5$, $R^6$, $R^7$ and $R^8$ have the definition as described for formula (I). Preferred definitions of $R^3$, $R^4$, $R^5$, $R^6$, $R^7$ and $R^8$ are as defined for formula (I).

The invention also relates to compounds of formula I-5:

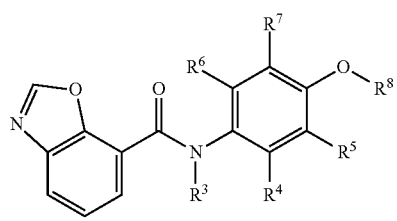

(I-5)

wherein $R^3$, $R^4$, $R^5$, $R^6$, $R^7$ and $R^8$ have the definition as described for formula (I). Preferred definitions of $R^3$, $R^4$, $R^5$, $R^6$, $R^7$ and $R^8$ are as defined for formula (I).

The invention also relates to compounds of formula I-6:

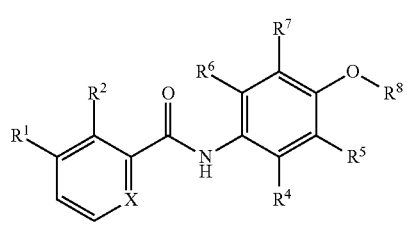

(I-6)

wherein $R^1$, $R^2$, $R^4$, $R^5$, $R^6$, $R^7$, $R^8$ and X have the definition as described for formula (I). Preferred definitions of $R^1$, $R^2$, $R^4$, $R^5$, $R^6$, $R^7$, $R^8$ and X are as defined for formula (I).

The invention also relates to compounds of formula I-7:

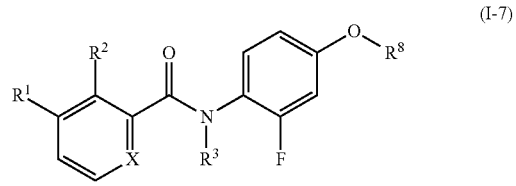

(I-7)

wherein $R^1$, $R^2$, $R^3$, $R^8$ and X have the definition as described for formula (I). Preferred definitions of $R^1$, $R^2$, $R^3$, $R^8$ and X are as defined for formula (I).

Further preferred embodiments of the present invention are the embodiments E-I.a to E-I.t, which are defined as compounds of formula (I) which are represented by one formula selected from the group consisting of the formula (I.a) to (I.t) as described below, wherein in formulae (I.a) to (I.t) the meanings of the substituents $R^3$, $R^4$, $R^5$, $R^6$, $R^7$ and $R^8$ have the preferred meanings as mentioned above or one of the meanings 1 to 300 given in the corresponding Table 1.

For example, embodiment E-I.a is represented by the compounds of formula (I.a)

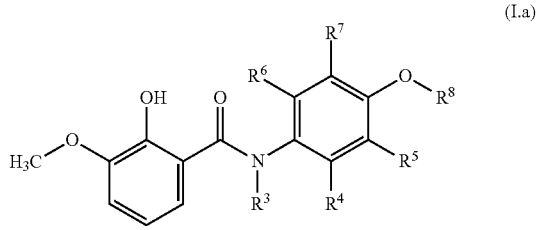

(I.a)

and the substituents $R^3$, $R^4$, $R^5$, $R^6$, $R^7$ and $R^8$ have the meanings as defined above or one of the meanings 1 to 300 given in the Table 1.

Embodiments E-I.b to E-I.t are defined accordingly and the substituents $R^3$, $R^4$, $R^5$, $R^6$, $R^7$ and $R^8$ have the meanings as defined above or one of the meanings 1 to 300 given in the corresponding Table 1.

Compounds of the present invention can be made as shown in the following schemes, in which, unless otherwise stated, the definition of each variable is as defined above for a compound of formula (I).

The compounds of formula (I-A) according to the invention, wherein $R^1$, $R^2$, $R^4$, $R^5$, $R^6$, $R^7$, $R^8$ and X are as defined for formula (I), can be obtained by transformation of a compound of formula (II), wherein $R^1$, $R^2$ and X are as defined for formula (I) and $R^{12}$ is hydroxyl, halogen or $C_1$-$C_6$alkoxy, with a compound of formula (III), wherein $R^4$, $R^5$, $R^6$, $R^7$ and $R^8$ are as defined for formula (I), and with a base or a peptide coupling reagent. This is shown in Scheme 1 below.

Scheme 1

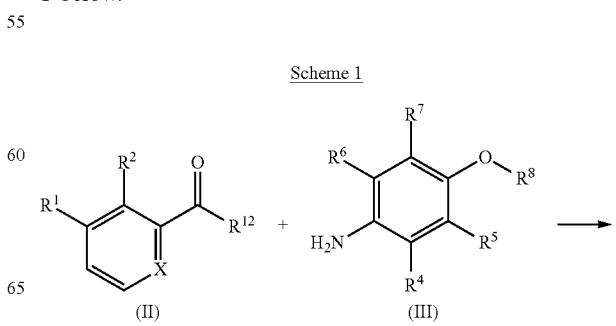

(II)     (III)

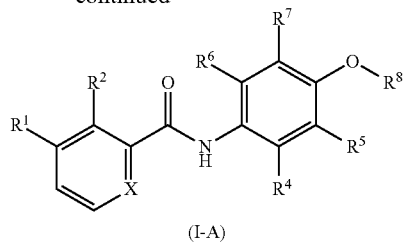

(I-A)

The compounds of formula (III), wherein $R^4$, $R^5$, $R^6$, $R^7$ and $R^8$ are as defined for formula (I), can be obtained by transformation of a compound of formula (IV), wherein $R^4$, $R^5$, $R^6$, $R^7$ and $R^8$ are as defined for formula (I), under reductive conditions, e.g. catalytic hydrogenation or with iron powder and hydrochloric acid. This is shown in Scheme 2 below.

Scheme 2

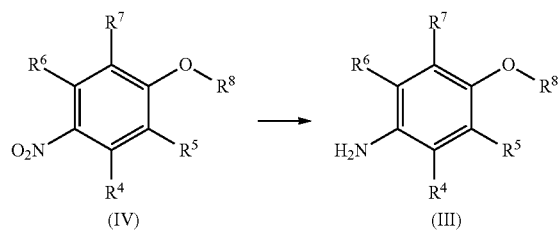

(IV) → (III)

The compounds of formula (IV), wherein $R^4$, $R^5$, $R^6$, $R^7$ and $R^8$ are as defined for formula (I), can be obtained by transformation of a compound of formula (V), wherein $R^4$, $R^5$, $R^6$ and $R^7$ are as defined for formula (I) with a compound of formula (VI), wherein $R^8$ is as defined for formula (I) and $R^{13}$ is hydroxyl, halogen, preferably chloro or bromo, or a sulfonate, preferably a mesylate with a base or under the conditions of the Mitsunobu reaction. This is shown in Scheme 3 below.

Scheme 3

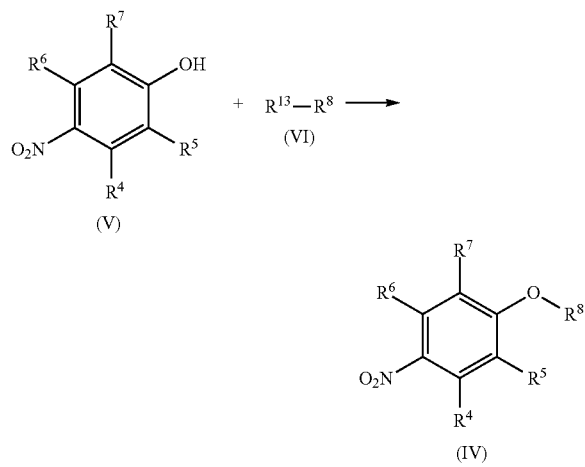

Alternatively, the compounds of formula (IV), wherein $R^4$, $R^5$, $R^6$, $R^7$ and $R^8$ are as defined for formula (I), can be obtained by transformation of a compound of formula (VII), wherein $R^4$, $R^5$, $R^6$ and $R^7$ are as defined for formula (I), with a compound of formula (VIII), wherein $R^8$ is as defined for formula (I) and with a base. This is shown in Scheme 4 below.

Scheme 4

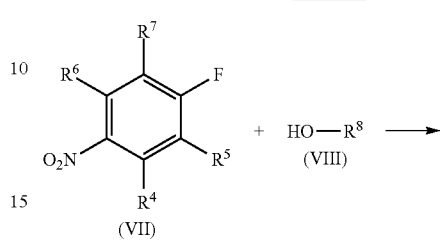

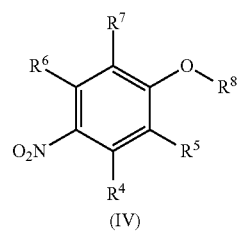

(IV)

Alternatively, the compounds of formula (I-A), wherein $R^1$, $R^2$, $R^4$, $R^5$, $R^6$, $R^7$, $R^8$ and X are as defined for formula (I), can be obtained by transformation of a compound of formula (IX), wherein $R^1$, $R^2$, $R^4$, $R^5$, $R^6$, $R^7$ and X are as defined for formula (I), with a compound of formula (VI), wherein $R^8$ is as defined for formula (I) and $R^{13}$ is hydroxyl, halogen, preferably chloro or bromo, or a sulfonate, preferably a mesylate with a base or under the conditions of the Mitsunobu reaction. This is shown in Scheme 5 below.

Scheme 5

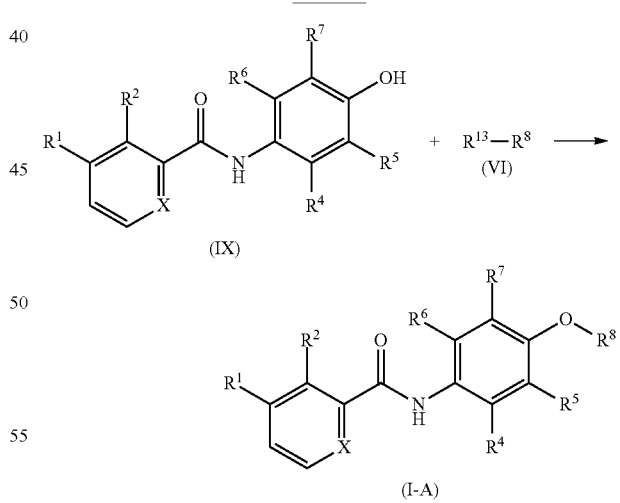

(I-A)

The compounds of formula (IX), wherein $R^1$, $R^2$, $R^4$, $R^5$, $R^6$, $R^7$ and X are as defined for formula (I) can be obtained by transformation of a compound of formula (II), wherein $R^1$, $R^2$ and X are as defined for formula (I) and $R^{12}$ is hydroxyl, halogen or $C_1$-$C_6$alkoxy, with a compound of formula (X), wherein $R^4$, $R^5$, $R^6$ and $R^7$ are as defined for formula (I) and with a base or a peptide coupling reagent. This is shown in Scheme 6 below.

Scheme 6

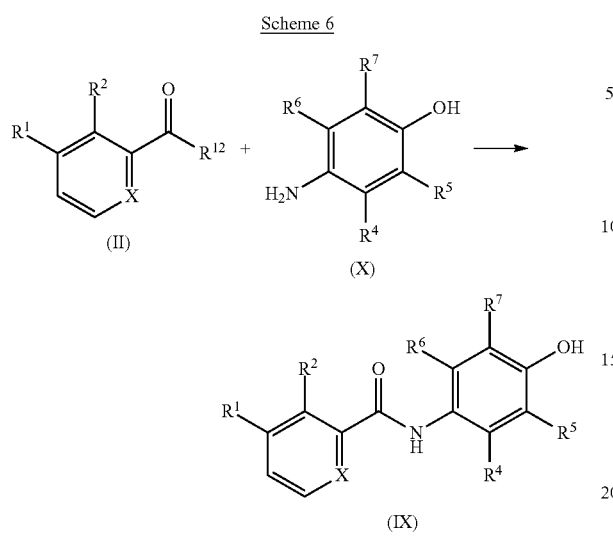

Alternatively, the compounds of formula (I-A), wherein $R^1$, $R^2$, $R^4$, $R^5$, $R^6$, $R^7$, $R^8$ and X are as defined for formula (I), can be obtained by transformation of a compound of formula (XI), wherein $R^1$, $R^2$, $R^4$, $R^5$, $R^6$, $R^7$ and X are as defined for formula (I), with a compound of formula (VIII), wherein $R^8$ is as defined for formula (I), and with a base. This is shown in Scheme 7 below.

Scheme 7

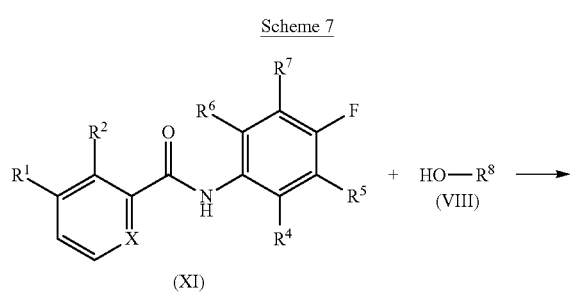

The compounds of formula (XI), wherein $R^1$, $R^2$, $R^4$, $R^5$, $R^6$, $R^7$ and X are as defined for formula (I), can be obtained by transformation of a compound of formula (II), wherein $R^1$, $R^2$ and X are as defined for formula (I) and $R^{12}$ is hydroxyl, halogen or $C_1$-$C_6$alkoxy, with a compound of formula (XII), wherein $R^4$, $R^5$, $R^6$ and $R^7$ are as defined for formula (I), and a base or a peptide coupling reagent. This is shown in Scheme 8 below.

Scheme 8

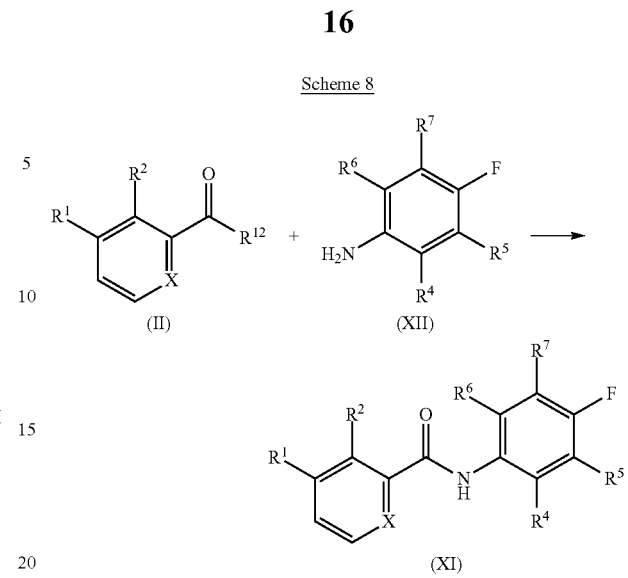

The compounds of formula (X), wherein $R^4$, $R^5$, $R^6$ and $R^7$ are as defined for formula (I), can be obtained by transformation of a compound of formula (V), wherein $R^4$, $R^5$, $R^6$ and $R^7$ are as defined for formula (I), under reductive conditions, e.g. catalytic hydrogenation or with iron powder and hydrochloric acid. This is shown in Scheme 9 below.

Scheme 9

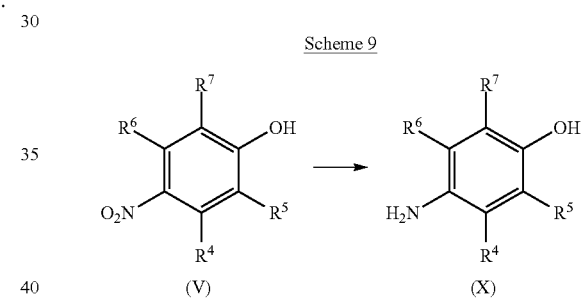

The compounds of formula (XII), wherein $R^4$, $R^5$, $R^6$ and $R^7$ are as defined for formula (I), can be obtained by transformation of a compound of formula (VII), wherein $R^4$, $R^5$, $R^6$ and $R^7$ are as defined for formula (I), under reductive conditions, e.g., catalytic hydrogenation or with iron powder and hydrochloric acid. This is shown in Scheme 10 below.

Scheme 10

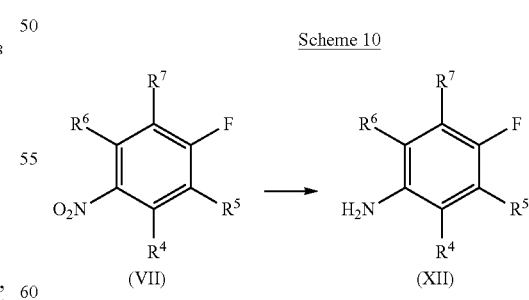

Surprisingly, it has now been found that the novel compounds of formula (I) have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use the compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (eg, rice), for the protection against fungal infections, as well as against phytopathogenic fungi occurring in the soil. The propagation material can be treated with a composition comprising a compound of formula (I) before planting: seed, eg, can be dressed before being sown.

The active ingredients according to the invention can also be applied to grains (coating), either by impregnating the seeds in a liquid formulation or by coating them with a solid formulation. The composition can also be applied to the planting site when the propagation material is being planted, eg, to the seed furrow during sowing. The invention relates also to such methods of treating plant propagation material and to the plant propagation material so treated.

Furthermore, the compounds according to present invention can be used for controlling fungi in related areas, for example in the protection of technical materials, including wood and wood related technical products, in food storage, in hygiene management.

In addition, the invention could be used to protect non-living materials from fungal attack, e.g., lumber, wall boards and paint.

The compounds of formula (I) may be, for example, effective against fungi and fungal vectors of disease as well as phytopathogenic bacteria and viruses. These fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp., *Stereum hirsutum, Thanatephorus cucumeris, Thielaviopsis basicola, Tilletia* spp, *Trichoderma* spp., including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins from Bacillus cereus or Bacillus popilliae; or insecticidal proteins from Bacillus thuringiensis, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably, said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following acyloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichlorophenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2, 5-dimethylphenoxymethyl)phenyl]-2-methoxy-iminoacetamide, 4-bromo-2-cyano-N,N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N, -dimethyl-5-p-tolylimidazole-1-sulfonamide, N-allyl-4, 5,-dimethyl-2-trimethylsilylthiophene-3-carboxamide, N—(I-cyano-1,2-dimethylpropyl)-2-(2, 4-dichlorophenoxy) propionamide, N-(2-methoxy-5-pyridyl)-cyclopropane carboxamide, (.+–.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenyl)phenyl]-3-methoxyacrylate, methyl (E)-2-[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-m ethoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-[(5-bromo-pyridin-2-yloxymethyl)phenyl]-3methoxyacrylate, methyl (E)-2-[2-(3-(3-iodopyridin-2yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2(5H)-furanone; 4,5-dichlorodithiazolinone, 4,5-benzodithiazolinone, 4,5-trimethylened ithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dicloran, dichlorophen, dichlozoline, diclobutrazol, diclocymet, diethofencarb, difenoconazole, difenzoquat, diflumetorim, O,O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneaminooxycarbonyl) amino]thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in WO 95/19363 or WO 04/72086, particularly the compounds disclosed therein.

Other examples of such biologically active compounds that the compounds of the invention may be used in combination with include but are not restricted to the following: Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorbenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

The following mixtures of the compounds of formula (I) with active ingredients are preferred. The abbreviation "TX" means one compound selected from the group of compounds 1.a.1-1.a.300 to 1.t.1-1.t.300 (Embodiments E-I.a to E-I.t) described in Table 1 or 2 (below).

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin 1 (696)+TX, cinerin 11 (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin 11 (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave*

(742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, 0,0,0',0'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloropralethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, benzovindiflupyr [1072957-71-1]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, oxathiapiprolin [1003318-67-9]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS, 12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11 Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; lancotrione [1486617-21-3]+TX, florpyrauxifen [943832-81-3]]+TX, ipfentrifluconazole [1417782-08-1]+TX, mefentrifluconazole [1417782-03-6]+TX, quinofumelin [861647-84-9]]+TX, chloroprallethrin [399572-87-3]]+TX, cyhalodiamide [1262605-53-7]]+TX, fluazaindolizine [1254304-22-7]+TX, fluxametamide [928783-29-3]+TX, epsilon-metofluthrin [240494-71-7]]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1] and kappa-tefluthrin [391634-71-2]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ®+TX, TAZO B®)+TX, *Azotobacter*+TX, *Azotobacter* chroocuccum (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus* chitinosporus strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* CrylAb+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis* kurstaki BMP 123 (Baritone®)+TX, *Bacillus thuringiensis* kurstaki HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Meloncont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Crypto-*

*coccus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, Halobacillus *trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces* farinosus+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+

TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX, Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, *Bugline cucumeris*®)+TX, *Amblyseius fallacis* (Fallacis®)+TX, *Amblyseius swirskii* (*Bugline swirskii*®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, Cephalonomia *stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, Eretmocerus *californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Sciarid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (TrichoStrip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names ", which is accessible on the internet [A. Wood; *Compendium of Pesticide Common Names*, Copyright® 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula (I) selected from a compound 1.a.1-1.a.300 to 1.t.1-1.t.300 described in Table 1 or 2 (below), and an active ingredient as described above are preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from one of compounds 1.a.1-1.a.300 to 1.t.1-1.t.300 described in Table 1 or 2 (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from a compound 1.a.1-1.a.300 to 1.t.1-1.t.300 described in Table 1 or 2 (below), and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds (I) for the preparation of these compositions are also a subject of the invention.

Another aspect of invention is related to the use of a compound of formula (I) or of a preferred individual compound as above-defined, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g., harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g., in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm, 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

EXAMPLES

Example 1

This Example Illustrates the Preparation of N-[4-(cyclohexoxy)phenyl]-3-hydroxy-4-methoxy-pyridine-2-carboxamide (Compound I.b.66)

a) Preparation of methyl 3-hydroxy-4-methoxy-pyridine-2-carboxylate

Concentrated sulfuric acid (1.4 ml, 27 mmol) was added dropwise to a suspension of 3-hydroxy-4-methoxy-pyridine-2-carboxylic acid (15 g, 89 mmol) in 375 ml of methanol. The reaction mixture was heated to reflux for 16 hours (h), then a further 1.4 ml of concentrated sulfuric acid was added. After heating the reaction mixture for further 24 h, another 1.4 ml of concentrated sulfuric acid was added. After heating the reaction mixture for a further 24 h, the mixture was cooled to room temperature. The solvent was removed under reduced pressure and the residue was taken up in water. This aqueous phase was brought to pH 8 by the addition of sodium bicarbonate and subsequently extracted with ethyl acetate. The organic layer was washed with brine, dried over sodium sulfate and evaporated under reduced pressure. The remainder was stirred in 70 ml of hexane for 30 minutes (min), filtered and dried to deliver methyl 3-hydroxy-4-methoxy-pyridine-2-carboxylate. M.p. 157-158° C. $^1$H-NMR (400 MHz, CDCl$_3$): δ=3.99 (s, 3H), 4.09 (s, 3H), 6.97 (d, 1H), 8.20 (d, 1H), 10.88 (bs, 1H).

b) Preparation of methyl 4-methoxy-3-[(4-methoxyphenyl)methoxy]pyridine-2-carboxylate Sodium hydride (1.8 g, 47 mmol) was added in portions to a solution of methyl 3-hydroxy-4-methoxy-pyridine-2-carboxylate (7.1 g, 39 mmol) in 100 ml of N,N-dimethylformamide at room temperature. The reaction mixture was stirred for 1 h at this temperature, and then 4-methoxybenzyl chloride (7.6 g, 47 mmol) was added. The reaction mixture was heated to 40° C. for 16 h, then cooled to room temperature, poured on water and extracted with ethyl acetate. The organic layer was washed with brine, dried over sodium sulfate and evaporated under reduced pressure. The remainder was purified by chromatography on silica gel, using ethyl acetate and heptane as eluents, to deliver methyl 4-methoxy-3-[(4-methoxyphenyl)methoxy]pyridine-2-carboxylate. $^1$H-NMR (400 MHz, CDCl$_3$): δ=3.82 (s, 3H), 3.93 (s, 3H), 3.96 (s, 3H), 5.05 (s, 2H), 6.89 (d, 2H), 6.97 (d, 1H), 7.41 (d, 2H), 8.32 (d, 1H).

c) Preparation of N-[4-(cyclohexoxy)phenyl]-3-hydroxy-4-methoxy-pyridine-2-carboxamide (Compound I.b.66)

Aluminum trimethanide (0.7 ml of a 2 M solution in heptane, 1.5 mmol) was added slowly to a solution of methyl 4-methoxy-3-[(4-methoxyphenyl)methoxy]pyridine-2-carboxylate (0.3 g, 1.0 mmol) and 4-(cyclohexoxy)aniline (0.2 g, 1.1 mmol) in 10 ml of toluene. The reaction mixture was stirred for 16 h at room temperature, then acidified by the addition of 20 ml of 2 N hydrochloric acid and stirred for further 30 min. After neutralization by the addition of saturated aqueous sodium bicarbonate solution, ethyl acetate was added and the mixture was filtered through Celite. The phases of the filtrate were separated and the aqueous phase was extracted with ethyl acetate. The combined organic layer was washed with brine, dried over sodium sulfate and evaporated under reduced pressure. The remainder was purified by chromatography on silica gel, using ethyl acetate and heptane as eluents, to deliver N-[4-(cyclohexoxy)phenyl]-3-hydroxy-4-methoxy-pyridine-2-carboxamide (Compound I.b.66). $^1$H-NMR (400 MHz, CDCl$_3$): δ=1.32-1.40 (m, 2H), 1.48-1.59 (m, 4H), 1.77-1.84 (m, 2H), 1.96-2.02 (m, 2H), 3.97 (s, 3H), 4.22 (q, 1H), 6.89-6.97 (m, 3H), 7.58 (d, 2H), 8.01 (d, 1H), 9.82 (s, 1H), 12.30 (s, 1H).

Example 2

This Example Illustrates the Preparation of N-[4-(4,4-dimethylcyclohexoxy)-2-fluoro-phenyl]-1,3-benzoxazole-7-carboxamide (Compound I.r.133)

a) Preparation of 4-(4,4-dimethylcyclohexoxy)-2-fluoro-1-nitro-benzene

Diisopropyl azodiformate (1.3 g, 6.1 mmol) was added dropwise to a solution of triphenylphosphine (1.6 g, 6.1 mmol), 3-fluoro-4-nitrophenol (1.0 g, 6.1 mmol) and 4,4-dimethylcyclohexanol (0.65 g, 5.1 mmol) in 20 ml of tetrahydrofuran. The reaction mixture was stirred for 16 h at room temperature, then diluted with ethyl acetate and water. The phases were separated, the organic layer was washed with water, dried over magnesium sulfate and evaporated under reduced pressure. The remainder was purified by chromatography on silica gel, using ethyl acetate and cyclohexane as eluents, to deliver 4-(4,4-dimethylcyclohexoxy)-2-fluoro-1-nitro-benzene. $^1$H-NMR (400 MHz, CDCl$_3$): δ=0.98 (s, 3H), 0.99 (s, 3H), 1.25-1.31 (m, 2H), 1.50-1.56 (m, 2H), 1.69-1.77 (m, 2H), 1.86-1.92 (m, 2H), 4.32 (q, 1H), 6.68-6.75 (m, 2H), 8.07 (t, 1H).

b) Preparation of 4-(4,4-dimethylcyclohexoxy)-2-fluoro-aniline 4-(4,4-Dimethylcyclohexoxy)-2-fluoro-1-nitro-benzene (0.8 g, 3.0 mmol) was dissolved in 15 ml of ethanol and stirred for 2 h at room temperature in the presence of hydrogen gas and catalytic amounts of 10% palladium on carbon. Subsequently the reaction mixture was filtered through Celite and rinsed with ethyl acetate. The solvents were removed under reduced pressure to deliver 4-(4,4-dimethylcyclohexoxy)-2-fluoro-aniline. $^1$H-NMR (400 MHz, CDCl$_3$): δ=0.94 (s, 3H), 0.98 (s, 3H), 1.20-1.29 (m, 2H), 1.43-1.68 (m, 4H), 1.78-1.89 (m, 2H), 3.43 (bs, 2H), 4.04 (q, 1H), 6.55 (dd, 1H), 6.61-6.71 (m, 2H).

c) Preparation of N-[4-(4,4-dimethylcyclohexoxy)-2-fluoro-phenyl]-1,3-benzoxazole-7-carboxamide (Compound I.r.133)

Triethylamine (0.45 g, 4.5 mmol) and 1-[bis(dimethylamino)methylene]-1H-1,2,3-triazolo[4,5-b]pyridinium-3-oxide hexafluorophosphate (0.51 g, 1.35 mmol) were added consecutively to a solution of 1,3-benzoxazole-7-carboxylic acid (0.15 g, 0.9 mmol) in 11 ml of acetonitrile. The mixture was stirred for 15 min at room temperature and then 4-(4,4-dimethylcyclohexoxy)-2-fluoro-aniline (0.21 g, 0.9 mmol) was added. The reaction mixture was stirred for 16 h at room temperature and then diluted with chloroform. Isolute was added to the mixture, then all volatiles were removed under reduced pressure, the remaining powder was placed on top of a chromatography column and purified by chromatography on silica gel, using ethyl acetate and heptane as eluents, to deliver N-[4-(4,4-dimethylcyclohexoxy)-2-fluoro-phenyl]-1,3-benzoxazole-7-carboxamide (compound I.r.133). $^1$H-NMR (400 MHz, CDCl$_3$): δ=0.99 (s, 3H), 1.01 (s, 3H), 1.27-1.35 (m, 2H), 1.52-1.60 (m, 2H), 1.68-1.79 (m, 2H), 1.87-1.96 (m, 2H), 4.25 (q, 1H), 6.79 (d, 2H), 7.59 (t, 1H), 8.04 (d, 1H), 8.28-8.33 (m, 2H), 8.39 (t, 1H), 8.99 (bs, 1H).

Table 1 below illustrates examples of individual compounds of formula (I) according to the invention.

TABLE 1

Individual compounds (1.a.1-1.a.300 to 1.t.1-1.t.300) of formula (I) according to the invention.

| Compound No. | $R^3$ | $R^4$ | $R^5$ | $R^6$ | $R^7$ | $R^8$ |
|---|---|---|---|---|---|---|
| 1 | H | H | H | H | H |  |
| 2 | OCH$_3$ | H | H | H | H |  |
| 3 | H | F | H | H | H |  |
| 4 | H | F | F | H | H |  |

TABLE 1-continued

Individual compounds (1.a.1-1.a.300 to 1.t.1-1.t.300) of formula (I) according to the invention.

| Compound No. | R³ | R⁴ | R⁵ | R⁶ | R⁷ | R⁸ |
|---|---|---|---|---|---|---|
| 5 | H | Cl | H | H | H | cyclopropyl |
| 6 | H | H | H | H | H | 2,2-dichloro-1-methylcyclopropyl |
| 7 | OCH₃ | H | H | H | H | 2,2-dichloro-1-methylcyclopropyl |
| 8 | H | F | H | H | H | 2,2-dichloro-1-methylcyclopropyl |
| 9 | H | F | F | H | H | 2,2-dichloro-1-methylcyclopropyl |
| 10 | H | Cl | H | H | H | 2,2-dichloro-1-methylcyclopropyl |
| 11 | H | H | H | H | H | 2-methyl-1-methylcyclopropyl |
| 12 | OCH₃ | H | H | H | H | 2-methyl-1-methylcyclopropyl |
| 13 | H | F | H | H | H | 2-methyl-1-methylcyclopropyl |
| 14 | H | F | F | H | H | 2-methyl-1-methylcyclopropyl |
| 15 | H | Cl | H | H | H | 2-methyl-1-methylcyclopropyl |
| 16 | H | H | H | H | H | 1-phenylcyclopropyl |
| 17 | OCH₃ | H | H | H | H | 1-phenylcyclopropyl |
| 18 | H | F | H | H | H | 1-phenylcyclopropyl |
| 19 | H | F | F | H | H | 1-phenylcyclopropyl |
| 20 | H | Cl | H | H | H | 1-phenylcyclopropyl |
| 21 | H | H | H | H | H | 1-benzylcyclopropyl |
| 22 | OCH₃ | H | H | H | H | 1-benzylcyclopropyl |
| 23 | H | F | H | H | H | 1-benzylcyclopropyl |
| 24 | H | F | F | H | H | 1-benzylcyclopropyl |
| 25 | H | Cl | H | H | H | 1-benzylcyclopropyl |
| 26 | H | H | H | H | H | cyclobutyl |
| 27 | OCH₃ | H | H | H | H | cyclobutyl |
| 28 | H | F | H | H | H | cyclobutyl |
| 29 | H | F | F | H | H | cyclobutyl |
| 30 | H | Cl | H | H | H | cyclobutyl |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 31 | H | H | H | H | H | 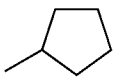 |
| 32 | OCH₃ | H | H | H | H | 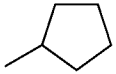 |
| 33 | H | F | H | H | H | 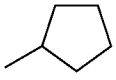 |
| 34 | H | F | F | H | H | 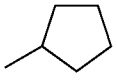 |
| 35 | H | Cl | H | H | H | 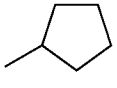 |
| 36 | H | H | H | H | H | 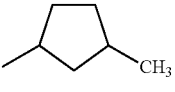 |
| 37 | OCH₃ | H | H | H | H | 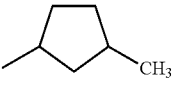 |
| 38 | H | F | H | H | H | 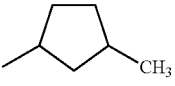 |
| 39 | H | F | F | H | H | 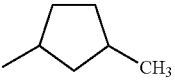 |
| 40 | H | Cl | H | H | H | 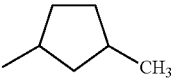 |
| 41 | H | H | H | H | H | 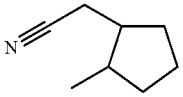 |
| 42 | OCH₃ | H | H | H | H | 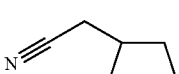 |
| 43 | H | F | H | H | H | 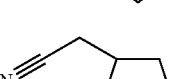 |
| 44 | H | F | F | H | H | 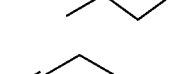 |
| 45 | H | Cl | H | H | H | 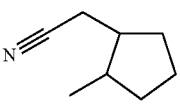 |
| 46 | H | H | H | H | H | 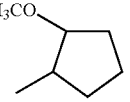 |
| 47 | OCH₃ | H | H | H | H | 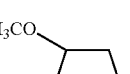 |
| 48 | H | F | H | H | H | 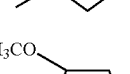 |
| 49 | H | F | F | H | H | 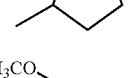 |
| 50 | H | Cl | H | H | H | 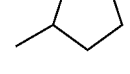 |
| 51 | H | H | H | H | H | 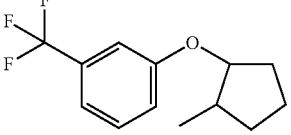 |
| 52 | OCH₃ | H | H | H | H | 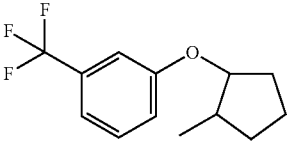 |
| 53 | H | F | H | H | H | 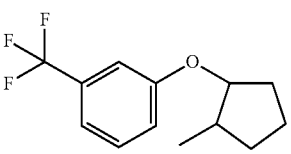 |
| 54 | H | F | F | H | H | 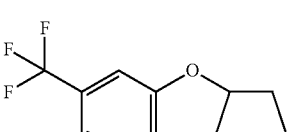 |
| 55 | H | Cl | H | H | H | 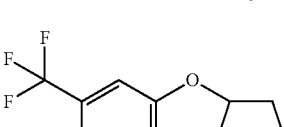 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 56 | H | H | H | H | H | 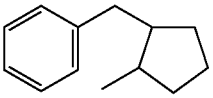 |
| 57 | OCH₃ | H | H | H | H | 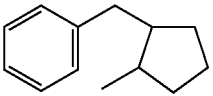 |
| 58 | H | F | H | H | H | 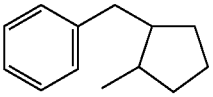 |
| 59 | H | F | F | H | H | 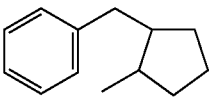 |
| 60 | H | Cl | H | H | H | 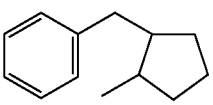 |
| 61 | H | H | H | H | H | 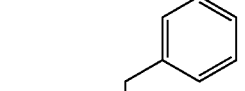 |
| 62 | OCH₃ | H | H | H | H | 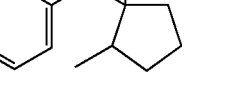 |
| 63 | H | F | H | H | H | 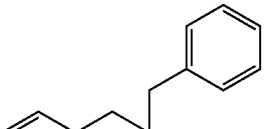 |
| 64 | H | F | F | H | H | 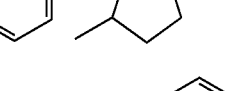 |
| 65 | H | Cl | H | H | H | 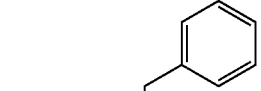 |
| 66 | H | H | H | H | H | 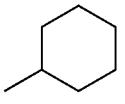 |
| 67 | OCH₃ | H | H | H | H | 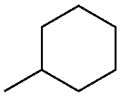 |
| 68 | H | F | H | H | H | 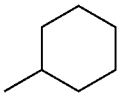 |
| 69 | H | F | F | H | H | 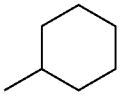 |
| 70 | H | Cl | H | H | H | 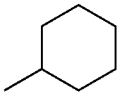 |
| 71 | H | H | H | H | H | 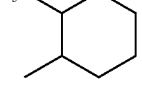 |
| 72 | OCH₃ | H | H | H | H | 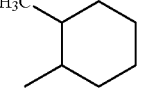 |
| 73 | H | F | H | H | H | 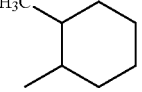 |
| 74 | H | F | F | H | H | 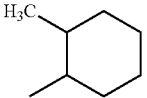 |
| 75 | H | Cl | H | H | H | 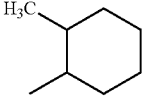 |
| 76 | H | H | H | H | H | 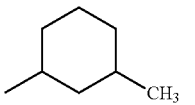 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 77 | OCH₃ | H | H | H | H | 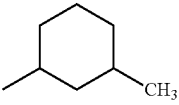 |
| 78 | H | F | H | H | H | 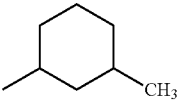 |
| 79 | H | F | F | H | H | 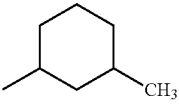 |
| 80 | H | Cl | H | H | H | 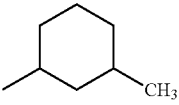 |
| 81 | H | H | H | H | H | 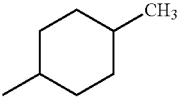 |
| 82 | OCH₃ | H | H | H | H | 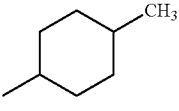 |
| 83 | H | F | H | H | H | 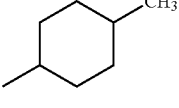 |
| 84 | H | F | F | H | H | 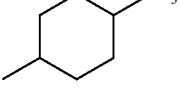 |
| 85 | H | Cl | H | H | H | 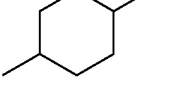 |
| 86 | H | H | H | H | H | 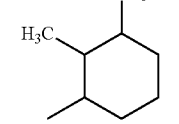 |
| 87 | OCH₃ | H | H | H | H | 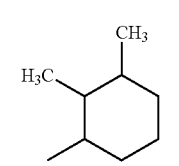 |
| 88 | H | F | H | H | H | 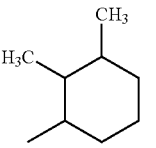 |
| 89 | H | F | F | H | H | 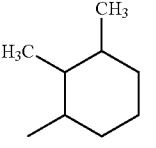 |
| 90 | H | Cl | H | H | H | 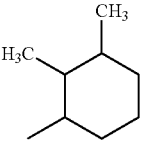 |
| 91 | H | H | H | H | H | 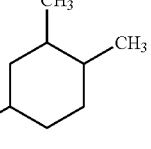 |
| 92 | OCH₃ | H | H | H | H | 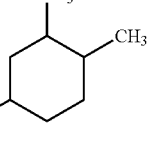 |
| 93 | H | F | H | H | H | 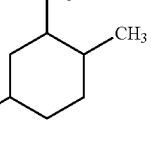 |
| 94 | H | F | F | H | H | 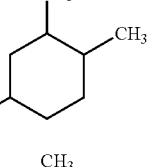 |
| 95 | H | Cl | H | H | H | 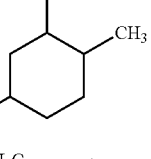 |
| 96 | H | H | H | H | H | 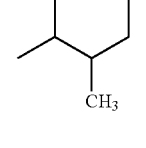 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 97 | OCH₃ | H | H | H | H | 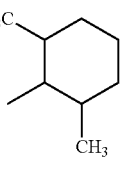 |
| 98 | H | F | H | H | H | 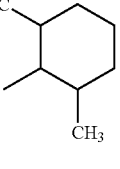 |
| 99 | H | F | F | H | H | 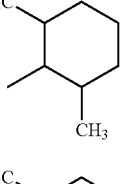 |
| 100 | H | Cl | H | H | H | 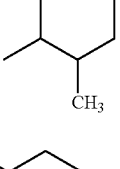 |
| 101 | H | H | H | H | H | 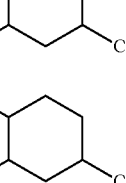 |
| 102 | OCH₃ | H | H | H | H |  |
| 103 | H | F | H | H | H | 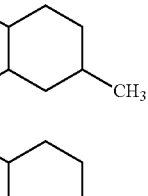 |
| 104 | H | F | F | H | H | 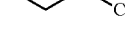 |
| 105 | H | Cl | H | H | H | 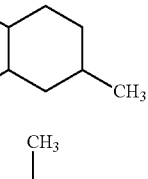 |
| 106 | H | H | H | H | H | 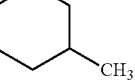 |
| 107 | OCH₃ | H | H | H | H | 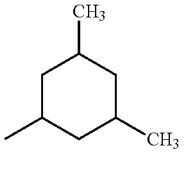 |
| 108 | H | F | H | H | H | 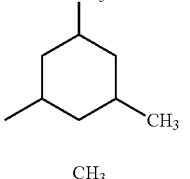 |
| 109 | H | F | F | H | H | 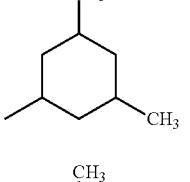 |
| 110 | H | Cl | H | H | H | 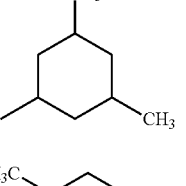 |
| 111 | H | H | H | H | H | 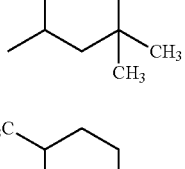 |
| 112 | OCH₃ | H | H | H | H | 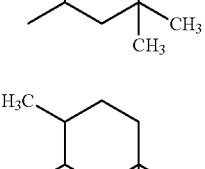 |
| 113 | H | F | H | H | H | 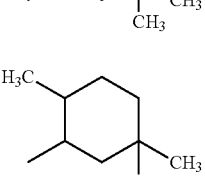 |
| 114 | H | F | F | H | H | 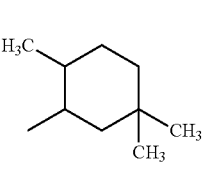 |
| 115 | H | Cl | H | H | H |  |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 116 | H | H | H | H | H | 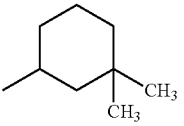 |
| 117 | OCH₃ | H | H | H | H | 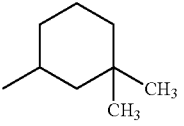 |
| 118 | H | F | H | H | H | 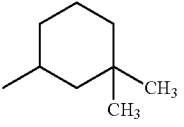 |
| 119 | H | F | F | H | H | 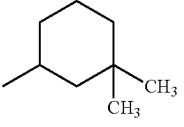 |
| 120 | H | Cl | H | H | H | 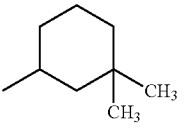 |
| 121 | H | H | H | H | H | 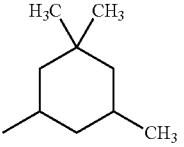 |
| 122 | OCH₃ | H | H | H | H | 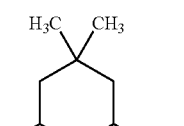 |
| 123 | H | F | H | H | H | 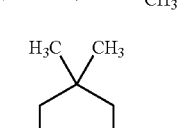 |
| 124 | H | F | F | H | H | 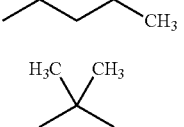 |
| 125 | H | Cl | H | H | H | 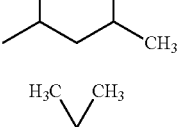 |
| 126 | H | H | H | H | H | 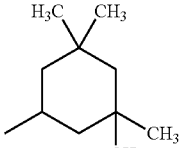 |
| 127 | OCH₃ | H | H | H | H | 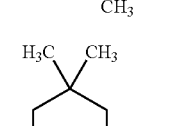 |
| 128 | H | F | H | H | H | 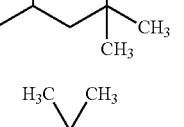 |
| 129 | H | F | F | H | H | 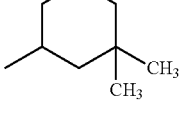 |
| 130 | H | Cl | H | H | H | 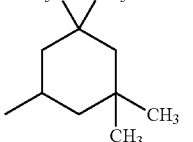 |
| 131 | H | H | H | H | H | 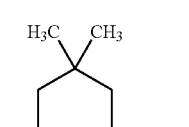 |
| 132 | OCH₃ | H | H | H | H | 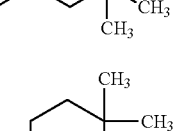 |
| 133 | H | F | H | H | H | 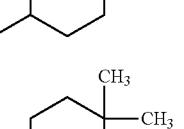 |
| 134 | H | F | F | H | H | 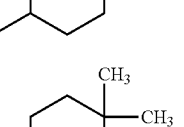 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 135 | H | Cl | H | H | H | 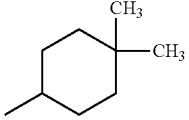 |
| 136 | H | H | H | H | H | 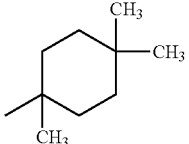 |
| 137 | OCH₃ | H | H | H | H | 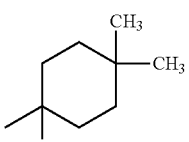 |
| 138 | H | F | H | H | H | 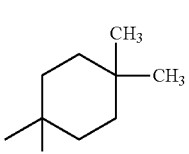 |
| 139 | H | F | F | H | H | 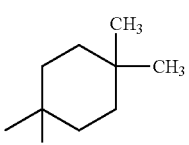 |
| 140 | H | Cl | H | H | H | 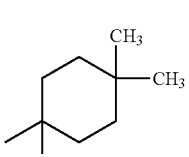 |
| 141 | H | H | H | H | H | 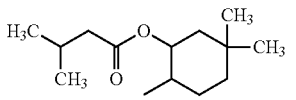 |
| 142 | OCH₃ | H | H | H | H | 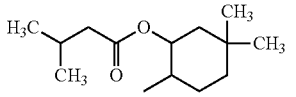 |
| 143 | H | F | H | H | H | 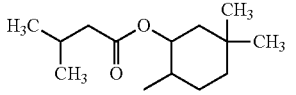 |
| 144 | H | F | F | H | H | 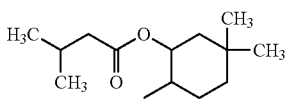 |
| 145 | H | Cl | H | H | H | 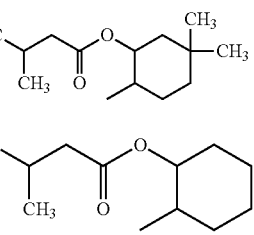 |
| 146 | H | H | H | H | H | 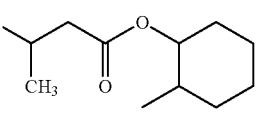 |
| 147 | OCH₃ | H | H | H | H | 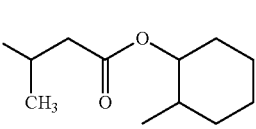 |
| 148 | H | F | H | H | H | 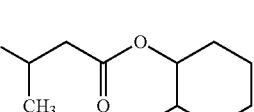 |
| 149 | H | F | F | H | H | 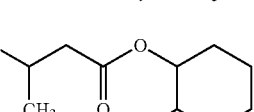 |
| 150 | H | Cl | H | H | H | 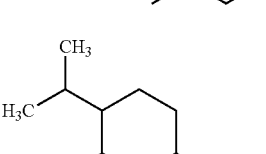 |
| 151 | H | H | H | H | H | 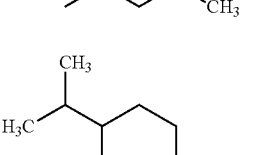 |
| 152 | OCH₃ | H | H | H | H | 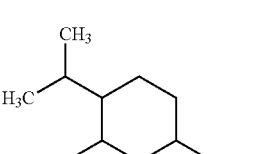 |
| 153 | H | F | H | H | H | 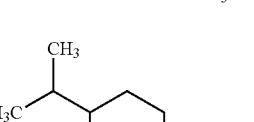 |
| 154 | H | F | F | H | H | |

TABLE 1-continued

Individual compounds (1.a.1-1.a.300 to 1.t.1-1.t.300) of formula (I) according to the invention.

| Compound No. | R³ | R⁴ | R⁵ | R⁶ | R⁷ | R⁸ |
|---|---|---|---|---|---|---|
| 155 | H | Cl | H | H | H | (1-methylethyl)-2,4-dimethylcyclohexyl |
| 156 | H | H | H | H | H | 4-(prop-1-en-2-yl)-2-methyl-1-methylcyclohexyl |
| 157 | OCH₃ | H | H | H | H | 4-(prop-1-en-2-yl)-2-methyl-1-methylcyclohexyl |
| 158 | H | F | H | H | H | 4-(prop-1-en-2-yl)-2-methyl-1-methylcyclohexyl |
| 159 | H | F | F | H | H | 4-(prop-1-en-2-yl)-2-methyl-1-methylcyclohexyl |
| 160 | H | Cl | H | H | H | 4-(prop-1-en-2-yl)-2-methyl-1-methylcyclohexyl |
| 161 | H | H | H | H | H | 2-ethyl-1-methylcyclohexyl |
| 162 | OCH₃ | H | H | H | H | 2-ethyl-1-methylcyclohexyl |
| 163 | H | F | H | H | H | 2-ethyl-1-methylcyclohexyl |
| 164 | H | F | F | H | H | 2-ethyl-1-methylcyclohexyl |
| 165 | H | Cl | H | H | H | 2-ethyl-1-methylcyclohexyl |
| 166 | H | H | H | H | H | 4-ethyl-1-methylcyclohexyl |
| 167 | OCH₃ | H | H | H | H | 4-ethyl-1-methylcyclohexyl |
| 168 | H | F | H | H | H | 4-ethyl-1-methylcyclohexyl |
| 169 | H | F | F | H | H | 4-ethyl-1-methylcyclohexyl |
| 170 | H | Cl | H | H | H | 4-ethyl-1-methylcyclohexyl |
| 171 | H | H | H | H | H | 4-(1-methylethyl)-1-methylcyclohexyl |
| 172 | OCH₃ | H | H | H | H | 4-(1-methylethyl)-1-methylcyclohexyl |
| 173 | H | F | H | H | H | 4-(1-methylethyl)-1-methylcyclohexyl |
| 174 | H | F | F | H | H | 4-(1-methylethyl)-1-methylcyclohexyl |
| 175 | H | Cl | H | H | H | 4-(1-methylethyl)-1-methylcyclohexyl |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 176 | H | H | H | H | H | 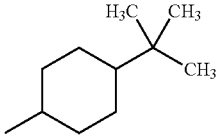 |
| 177 | OCH₃ | H | H | H | H | 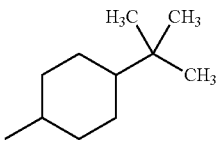 |
| 178 | H | F | H | H | H | 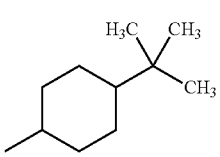 |
| 179 | H | F | F | H | H | 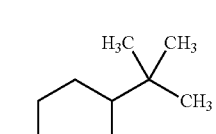 |
| 180 | H | Cl | H | H | H | 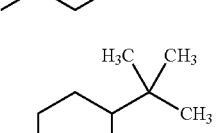 |
| 181 | H | H | H | H | H | 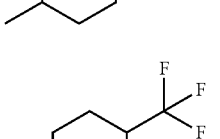 |
| 182 | OCH₃ | H | H | H | H | 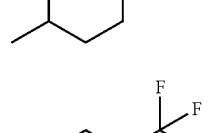 |
| 183 | H | F | H | H | H | 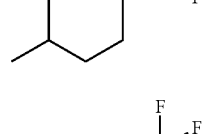 |
| 184 | H | F | F | H | H | 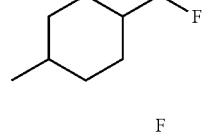 |
| 185 | H | Cl | H | H | H | 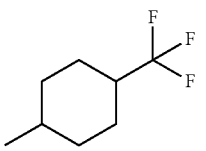 |
| 186 | H | H | H | H | H | 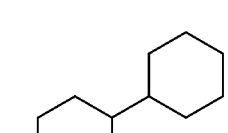 |
| 187 | OCH₃ | H | H | H | H | 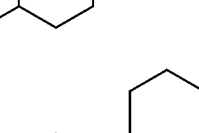 |
| 188 | H | F | H | H | H | 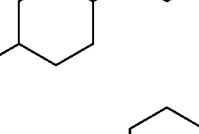 |
| 189 | H | F | F | H | H | 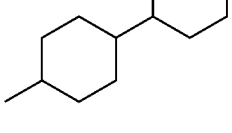 |
| 190 | H | Cl | H | H | H | 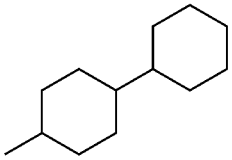 |
| 191 | H | H | H | H | H | 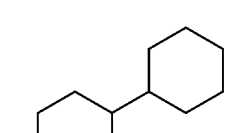 |
| 192 | OCH₃ | H | H | H | H | 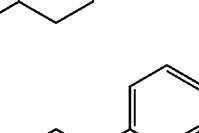 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 193 | H | F | H | H | H | 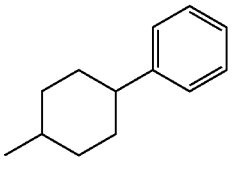 |
| 194 | H | F | F | H | H | 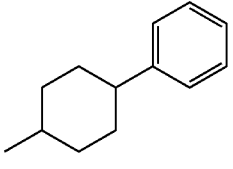 |
| 195 | H | Cl | H | H | H | 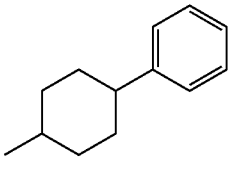 |
| 196 | H | H | H | H | H | 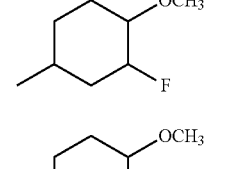 |
| 197 | OCH₃ | H | H | H | H | 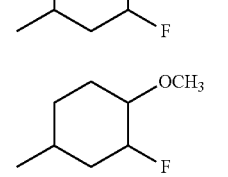 |
| 198 | H | F | H | H | H | 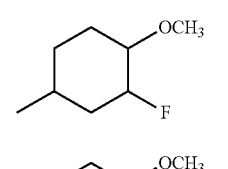 |
| 199 | H | F | F | H | H | 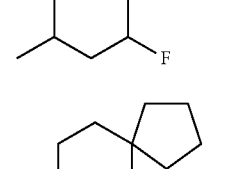 |
| 200 | H | Cl | H | H | H | 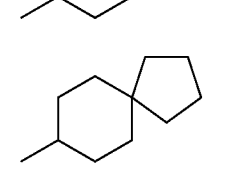 |
| 201 | H | H | H | H | H |  |
| 202 | OCH₃ | H | H | H | H | 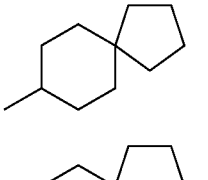 |
| 203 | H | F | H | H | H | 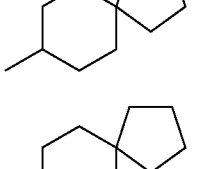 |
| 204 | H | F | F | H | H | 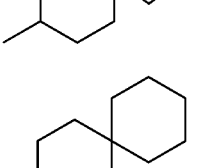 |
| 205 | H | Cl | H | H | H | 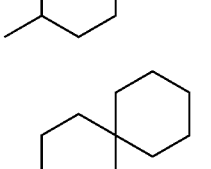 |
| 206 | H | H | H | H | H | 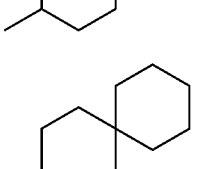 |
| 207 | OCH₃ | H | H | H | H | 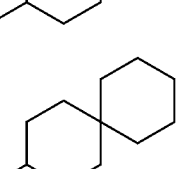 |
| 208 | H | F | H | H | H | 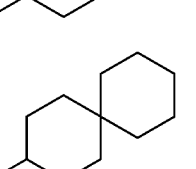 |
| 209 | H | F | F | H | H | 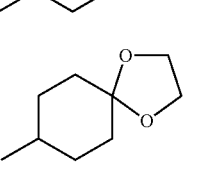 |
| 210 | H | Cl | H | H | H | 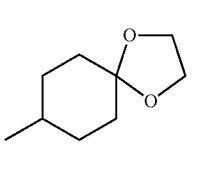 |
| 211 | H | H | H | H | H |  |
| 212 | OCH₃ | H | H | H | H | |

TABLE 1-continued

Individual compounds (1.a.1-1.a.300 to 1.t.1-1.t.300) of formula (I) according to the invention.

| Compound No. | R³ | R⁴ | R⁵ | R⁶ | R⁷ | R⁸ |
|---|---|---|---|---|---|---|
| 213 | H | F | H | H | H | |
| 214 | H | F | F | H | H | |
| 215 | H | Cl | H | H | H | |
| 216 | H | H | H | H | H | |
| 217 | OCH₃ | H | H | H | H | |
| 218 | H | F | H | H | H | |
| 219 | H | F | F | H | H | |
| 220 | H | Cl | H | H | H | |
| 221 | H | H | H | H | H | |
| 222 | OCH₃ | H | H | H | H | |
| 223 | H | F | H | H | H | |
| 224 | H | F | F | H | H | |
| 225 | H | Cl | H | H | H | |
| 226 | H | H | H | H | H | |
| 227 | OCH₃ | H | H | H | H | |
| 228 | H | F | H | H | H | |
| 229 | H | F | F | H | H | |
| 230 | H | Cl | H | H | H | |
| 231 | H | H | H | H | H | |
| 232 | OCH₃ | H | H | H | H | |
| 233 | H | F | H | H | H | |
| 234 | H | F | F | H | H | |
| 235 | H | Cl | H | H | H | |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 236 | H | H | H | H | H | 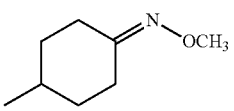 |
| 237 | OCH₃ | H | H | H | H | 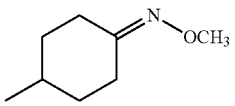 |
| 238 | H | F | H | H | H | 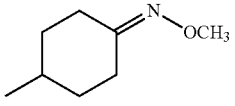 |
| 239 | H | F | F | H | H | 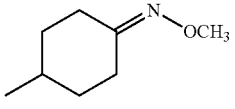 |
| 240 | H | Cl | H | H | H | 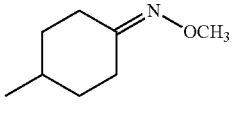 |
| 241 | H | H | H | H | H | 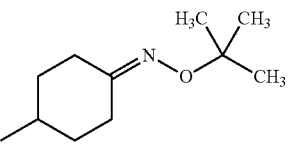 |
| 242 | OCH₃ | H | H | H | H | 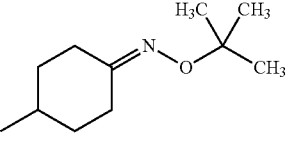 |
| 243 | H | F | H | H | H | 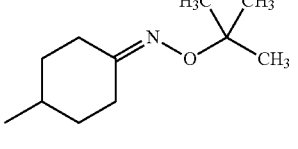 |
| 244 | H | F | F | H | H | 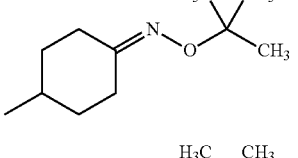 |
| 245 | H | Cl | H | H | H | 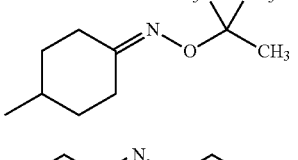 |
| 246 | H | H | H | H | H |  |
| 247 | OCH₃ | H | H | H | H | 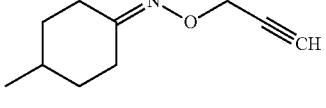 |
| 248 | H | F | H | H | H | 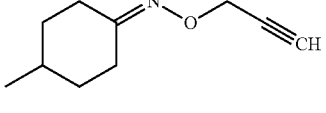 |
| 249 | H | F | F | H | H | 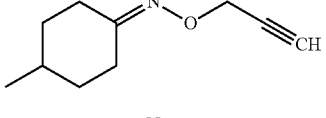 |
| 250 | H | Cl | H | H | H | 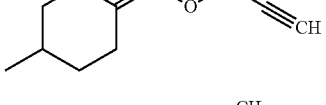 |
| 251 | H | H | H | H | H | 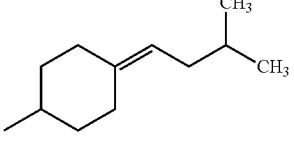 |
| 252 | OCH₃ | H | H | H | H | 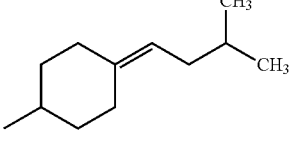 |
| 253 | H | F | H | H | H | 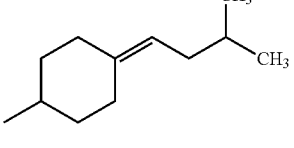 |
| 254 | H | F | F | H | H | 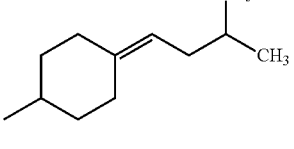 |
| 255 | H | Cl | H | H | H | 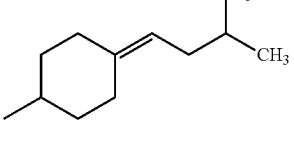 |
| 256 | H | H | H | H | H | 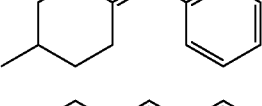 |
| 257 | OCH₃ | H | H | H | H | 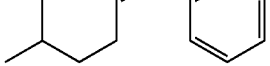 |

TABLE 1-continued
Individual compounds (1.a.1-1.a.300 to 1.t.1-1.t.300) of formula (I) according to the invention.
| Compound No. | R³ | R⁴ | R⁵ | R⁶ | R⁷ | R⁸ |
|---|---|---|---|---|---|---|
| 258 | H | F | H | H | H | 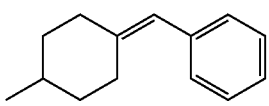 |
| 259 | H | F | F | H | H | 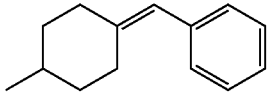 |
| 260 | H | Cl | H | H | H | 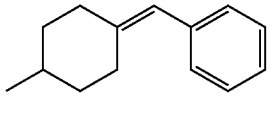 |
| 261 | H | H | H | H | H | 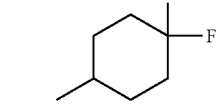 |
| 262 | OCH₃ | H | H | H | H | 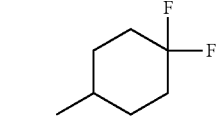 |
| 263 | H | F | H | H | H | 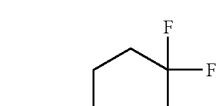 |
| 264 | H | F | F | H | H | 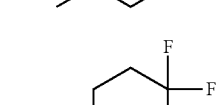 |
| 265 | H | Cl | H | H | H | 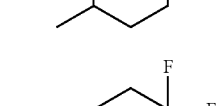 |
| 266 | H | H | H | H | H | 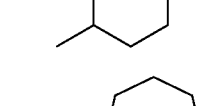 |
| 267 | OCH₃ | H | H | H | H | 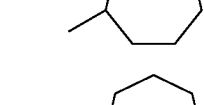 |
| 268 | H | F | H | H | H | 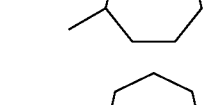 |
| 269 | H | F | F | H | H | 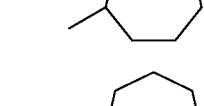 |
| 270 | H | Cl | H | H | H | 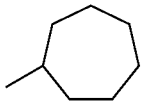 |
| 271 | H | H | H | H | H | 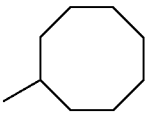 |
| 272 | OCH₃ | H | H | H | H | 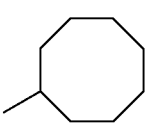 |
| 273 | H | F | H | H | H | 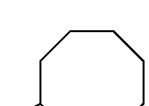 |
| 274 | H | F | F | H | H | 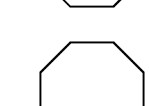 |
| 275 | H | Cl | H | H | H | 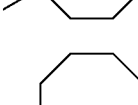 |
| 276 | H | H | H | H | H | 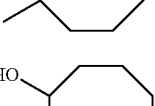 |
| 277 | OCH₃ | H | H | H | H | 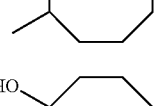 |
| 278 | H | F | H | H | H | 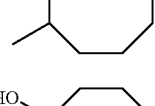 |
| 279 | H | F | F | H | H | 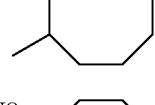 |
| 280 | H | Cl | H | H | H | 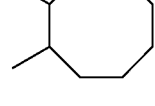 |

TABLE 1-continued

Individual compounds (1.a.1-1.a.300 to 1.t.1-1.t.300) of formula (I) according to the invention.

| Compound No. | R³ | R⁴ | R⁵ | R⁶ | R⁷ | R⁸ |
|---|---|---|---|---|---|---|
| 281 | H | H | H | H | H | isobutyryloxy-methylcyclooctyl |
| 282 | OCH₃ | H | H | H | H | isobutyryloxy-methylcyclooctyl |
| 283 | H | F | H | H | H | isobutyryloxy-methylcyclooctyl |
| 284 | H | F | F | H | H | isobutyryloxy-methylcyclooctyl |
| 285 | H | Cl | H | H | H | isobutyryloxy-methylcyclooctyl |
| 286 | H | H | H | H | H | hydroxy-methylcyclooctyl |
| 287 | OCH₃ | H | H | H | H | hydroxy-methylcyclooctyl |
| 288 | H | F | H | H | H | hydroxy-methylcyclooctyl |
| 289 | H | F | F | H | H | hydroxy-methylcyclooctyl |
| 290 | H | Cl | H | H | H | hydroxy-methylcyclooctyl |
| 291 | H | H | H | H | H | acetoxy-methylcyclooctyl |
| 292 | OCH₃ | H | H | H | H | acetoxy-methylcyclooctyl |
| 293 | H | F | H | H | H | acetoxy-methylcyclooctyl |
| 294 | H | F | F | H | H | acetoxy-methylcyclooctyl |
| 295 | H | Cl | H | H | H | acetoxy-methylcyclooctyl |
| 296 | H | H | H | H | H | methyl-oxaspiro[3.5]nonane |
| 297 | OCH₃ | H | H | H | H | methyl-oxaspiro[3.5]nonane |
| 298 | H | F | H | H | H | methyl-oxaspiro[3.5]nonane |
| 299 | H | F | F | H | H | methyl-oxaspiro[3.5]nonane |
| 300 | H | Cl | H | H | H | methyl-oxaspiro[3.5]nonane |

Wherein there are:

a) 300 compounds of formula (I.a):

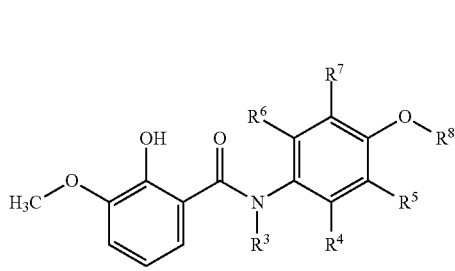

wherein $R^3$, $R^4$, $R^5$, $R^6$, $R^7$ and $R^8$ are as defined in Table 1.

b) 300 compounds of formula (I.b):

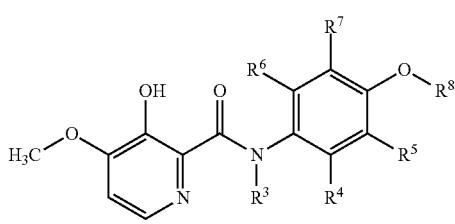

wherein $R^3$, $R^4$, $R^5$, $R^6$, $R^7$ and $R^8$ are as defined in Table 1, with the proviso that the compound of formula 1.I.b is not 3-hydroxy-4-methoxy-N-[4-(3,3,5,5-tetramethylcyclohexoxy)phenyl]pyridine-2-carboxamide.

c) 300 compounds of formula (I.c):

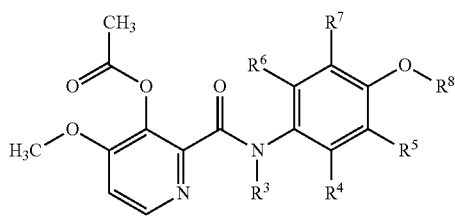

wherein $R^3$, $R^4$, $R^5$, $R^6$, $R^7$ and $R^8$ are as defined in Table 1.

d) 300 compounds of formula (I.d):

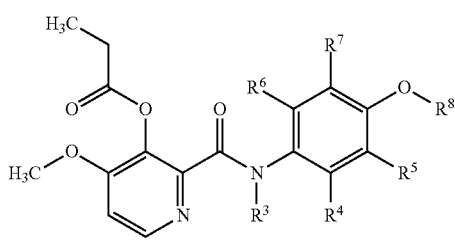

wherein $R^3$, $R^4$, $R^5$, $R^6$, $R^7$ and $R^8$ are as defined in Table 1.

e) 300 compounds of formula (I.e):

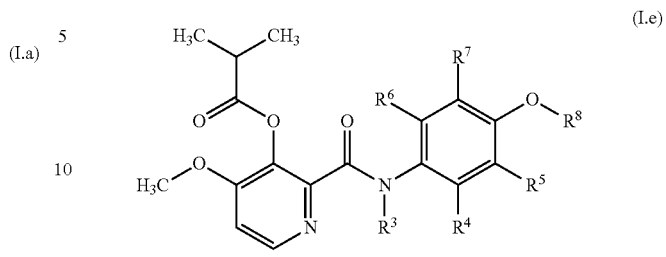

wherein $R^3$, $R^4$, $R^5$, $R^6$, $R^7$ and $R^8$ are as defined in Table 1.

f) 300 compounds of formula (I.f):

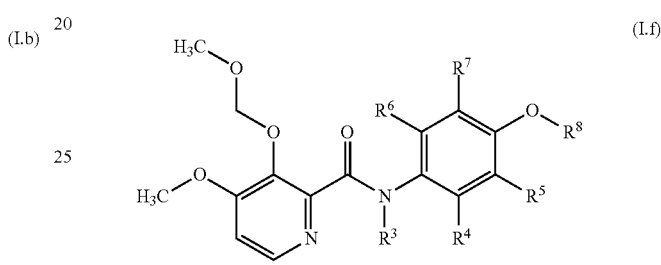

wherein $R^3$, $R^4$, $R^5$, $R^6$, $R^7$ and $R^8$ are as defined in Table 1.

g) 300 compounds of formula (I.g):

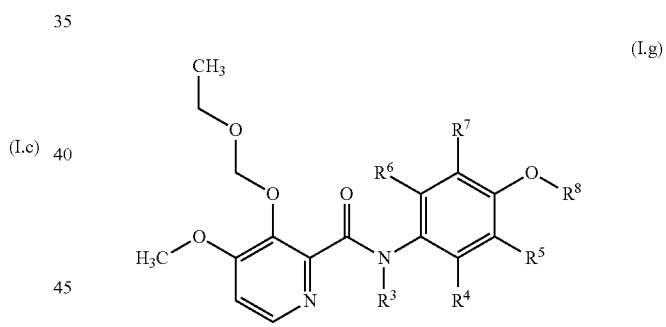

Wherein $R^3$, $R^4$, $R^5$, $R^6$, $R^7$ and $R^8$ are as defined in Table 1.

h) 300 compounds of formula (I.h):

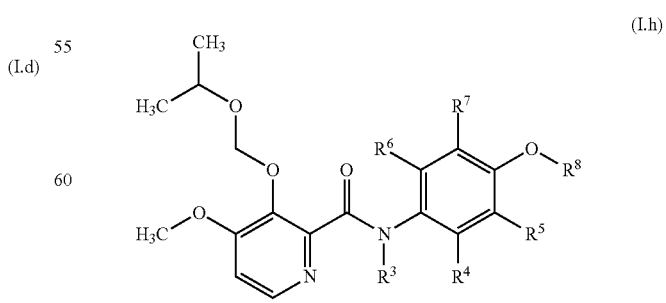

wherein $R^3$, $R^4$, $R^5$, $R^6$, $R^7$ and $R^8$ are as defined in Table 1.

i) 300 compounds of formula (I.i):

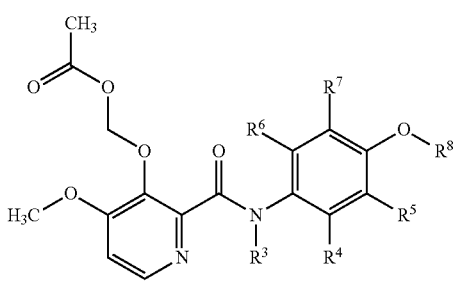

wherein $R^3$, $R^4$, $R^5$, $R^6$, $R^7$ and $R^8$ are as defined in Table 1.

j) 300 compounds of formula (I.j):

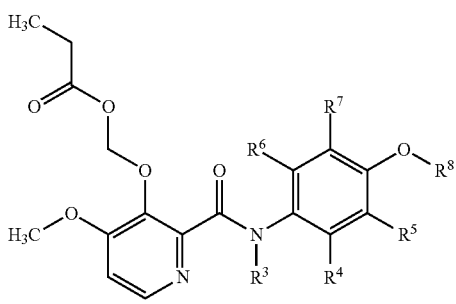

wherein $R^3$, $R^4$, $R^5$, $R^6$, $R^7$ and $R^8$ are as defined in Table 1.

k) 300 compounds of formula (I.k):

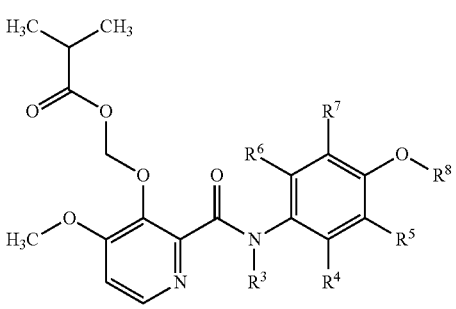

wherein $R^3$, $R^4$, $R^5$, $R^6$, $R^7$ and $R^8$ are as defined in Table 1.

m) 300 compounds of formula (I.m):

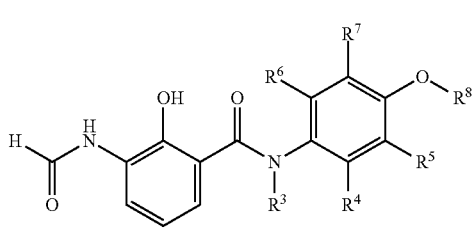

wherein $R^3$, $R^4$, $R^5$, $R^6$, $R^7$ and $R^8$ are as defined in Table 1.

n) 300 compounds of formula (I.n):

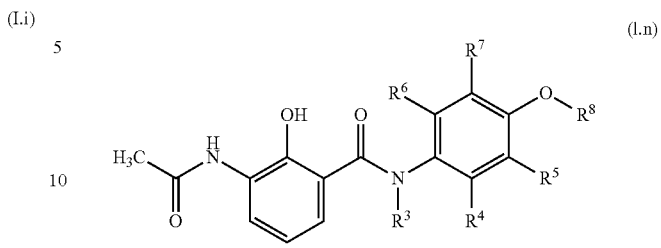

wherein $R^3$, $R^4$, $R^5$, $R^6$, $R^7$ and $R^8$ are as defined in Table 1.

o) 300 compounds of formula (I.o):

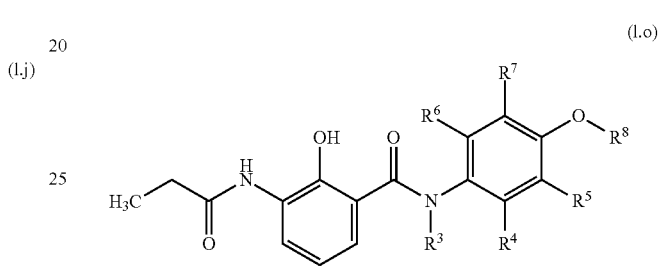

wherein $R^3$, $R^4$, $R^5$, $R^6$, $R^7$ and $R^8$ are as defined in Table 1.

p) 300 compounds of formula (I.p):

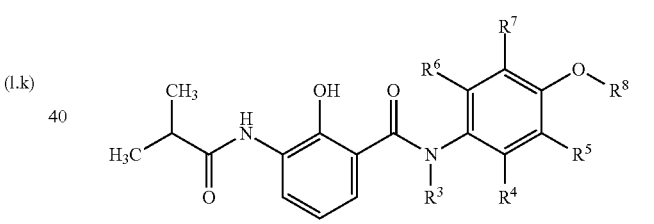

Wherein $R^3$, $R^4$, $R^5$, $R^6$, $R^7$ and $R^8$ are as defined in Table 1.

q) 300 compounds of formula (I.q):

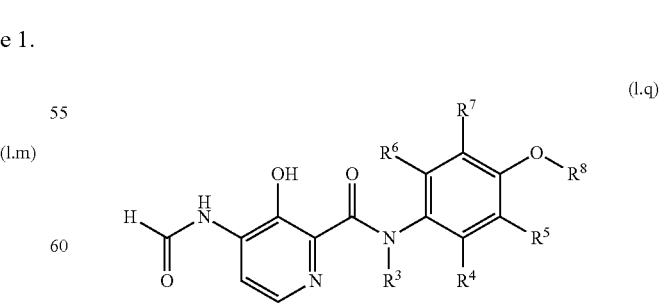

wherein $R^3$, $R^4$, $R^5$, $R^6$, $R^7$ and $R^8$ are as defined in Table 1.

r) 300 compounds of formula (I.r):

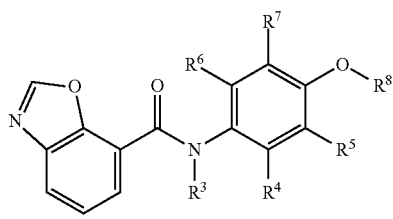

(I.r)

wherein $R^3$, $R^4$, $R^5$, $R^6$, $R^7$ and $R^8$ are as defined in Table 1.

s) 300 compounds of formula (I.s):

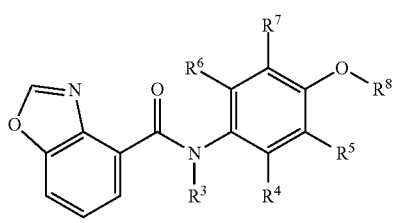

(I.s)

wherein $R^3$, $R^4$, $R^5$, $R^6$, $R^7$ and $R^8$ are as defined in Table 1.

t) 300 compounds of formula (I.t):

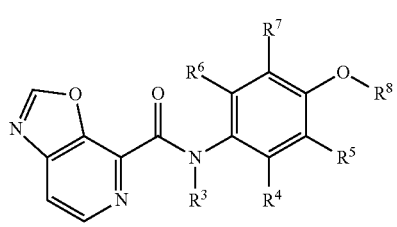

(I.t)

wherein $R^3$, $R^4$, $R^5$, $R^6$, $R^7$ and $R^8$ are as defined in Table 1.

Throughout this description, temperatures are given in degrees Celsius (° C.) and "m.p." means melting point. LC/MS means Liquid Chromatography Mass Spectrometry and the description of the apparatus and the method is: (ACQUITY UPLC from Waters, Phenomenex Gemini C18, 3 μm particle size, 110 Angström, 30×3 mm column, 1.7 mL/min., 60° C., $H_2O$+0.05% HCOOH (95%)/$CH_3CN$/MeOH 4:1+0.04% HCOOH (5%)–2 min.–$CH_3CN$/MeOH 4:1+0.04% HCOOH (5%)–0.8 min., ACQUITY SQD Mass Spectrometer from Waters, ionization method: electrospray (ESI), Polarity: positive ions, Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700)).

TABLE 2

Melting point and LC/MS data for selected compounds of Table 1.

| Compound no. | Melting point (° C.) | LC/MS Rt = Retention time |
|---|---|---|
| I.b.31 | 123-130 | |
| I.b.33 | 127-129 | |
| I.b.56 | | Rt = 1.27 min; MS: m/z = 419 (M + 1) |
| I.b.66 | 114-117 | |
| I.b.68 | 125-127 | |
| I.b.73 | 145-149 | |
| I.b.78 | 114-118 | |
| I.b.116 | 113-117 | |
| I.b.123 | 136-140 | |
| I.b.128 | | Rt = 1.37 min; MS: m/z = 417 (M + 1) |
| I.b.133 | | Rt = 1.29 min; MS: m/z = 389 (M + 1) |
| I.b.136 | 155-157 | |
| I.b.146 | 105-112 | |
| I.b.148 | | Rt = 1.21 min; MS: m/z = 461 (M + 1) |
| I.b.151 | 172-177 | |
| I.b.166 | 139-141 | |
| I.b.168 | 113-123 | |
| I.b.171 | 115-118 | |
| I.b.178 | | Rt = 1.39 min; MS: m/z = 417 (M + 1) |
| I.b.183 | 171-172 | |
| I.b.188 | | Rt = 1.48 min; MS: m/z = 443 (M + 1) |
| I.b.193 | | Rt = 1.28 min; MS: m/z = 435 (M + 1) |
| I.b.201 | 151-153 | |
| I.b.203 | 146-149 | |
| I.b.206 | | Rt = 1.41 min; MS: m/z = 411 (M + 1) |
| I.b.211 | | Rt = 0.94 min; MS: m/z = 401 (M + 1) |
| I.b.216 | 157-160 | |
| I.b.226 | | Rt = 0.82 min; MS: m/z = 357 (M + 1) |
| I.b.231 | | Rt = 1.14 min; MS: m/z = 355 (M + 1) |
| I.b.236 | | Rt = 0.97 min; MS: m/z = 386 (M + 1) |
| I.b.241 | | Rt = 1.22 min; MS: m/z = 428 (M + 1) |
| I.b.246 | | Rt = 1.00 min; MS: m/z = 410 (M + 1) |
| I.b.251 | | Rt = 1.38 min; MS: m/z = 411 (M + 1) |
| I.b.256 | | Rt = 1.28 min; MS: m/z = 431 (M + 1) |
| I.b.268 | | Rt = 1.24 min; MS: m/z = 375 (M + 1) |
| I.b.271 | | Rt = 1.26 min; MS: m/z = 371 (M + 1) |
| I.b.273 | | Rt = 1.29 min; MS: m/z = 389 (M + 1) |
| I.b.278 | 134-137 | |
| I.b.283 | | Rt = 2.12 min; MS: m/z = 476 (M + 1) |
| I.b.288 | | Rt = 1.27 min; MS: m/z = 405 (M + 1) |
| I.b.293 | 90-95 | |
| I.b.296 | 160-183 | |
| I.b.298 | 142-157 | |
| I.c.273 | 103-108 | |
| I.c.298 | 146-167 | |
| I.r.133 | 130-132 | |

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

Biological Examples

*Alternaria solani*/Tomato/Leaf Disc (Early Blight)

Tomato leaf disks cv. Baby are placed on agar in multiwell plates (24-well format) and sprayed with the test compound formulated with DMSO and Tween20 and diluted in water. The leaf disks are inoculated with a spore suspension of the fungus 2 days after application. The inoculated leaf disks are incubated at 23° C./21° C. (day/night) and 80% relative humidity (rh) under a light regime of 12/12 h (light/dark) in a climate cabinet and the activity of a compound is assessed as percent disease control compared to untreated when an appropriate level of disease damage appears on untreated check disk leaf disks (5-7 days after application).

Compounds I.b.66, I.b.133, 1.b.168 and I.c.273 at 200 ppm in the formulation gives at least 80% disease control in this test when compared to untreated control leaf disks under the same conditions, which show extensive disease development.

*Blumeria graminis* f. sp. *tritici* (*Erysiphe graminis* f. sp. *tritici*)/Wheat/Leaf Disc Preventative (Powdery Mildew on Wheat)

Wheat leaf segments cv. Kanzler are placed on agar in a multiwell plate (24-well format) and sprayed with the test compound formulated with DMSO and Tween20 and diluted in water. The leaf disks are inoculated by shaking powdery mildew infected plants above the test plates 1 day after application. The inoculated leaf disks are incubated at 20° C.

and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application).

Compounds I.b.133, I.b.268, I.c.273 and I.b.298 at 200 ppm in the formulation give at least 80% disease control in this test when compared to untreated control leaf disks under the same conditions, which show extensive disease development.

*Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

Compounds I.b.31, I.b.66, I.b.133, I.b.178, I.b.193, I.b.231, I.b.256, I.b.268, I.b.271, I.b.273, I.b.123, I.c.148, I.b.166, I.b.168, I.b.183, I.b.203, I.b.283, I.b.293 and I.b.298 at 200 ppm in the formulation give at least 80% disease control in this test when compared to untreated control leaf disks under the same conditions, which show extensive disease development.

*Fusarium culmorum*/Liquid Culture (Head Blight)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

Compound 1.b.193 and I.c.273 at 200 ppm in the formulation gives at least 80% disease control in this test when compared to untreated control leaf disks under the same conditions, which show extensive disease development.

*Gaeumannomyces graminis*/Liquid Culture (Take-all of Cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.b.31, I.b.66, I.b.128, I.b.133, I.b.178, I.b.188, I.b.193, I.b.211, I.b.231, I.b.236, I.b.241, I.b.246, I.b.251, I.b.256, I.b.268, I.b.271, I.b.273, I.b.33, I.b.68, I.b.73, I.b.123, I.c.148, I.b.151, I.b.166, I.b.168, I.b.183, I.b.201, I.b.203, I.b.283, I.b.288, I.b.293, I.b.298 and I.c.298 at 200 ppm in the formulation give at least 80% disease control in this test when compared to untreated control leaf disks under the same conditions, which show extensive disease development.

*Glomerella lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

Compounds I.b.31, I.b.66, I.b.128, I.b.133, I.b.178, I.b.193, I.b.231, I.b.241, I.b.246, I.b.251, I.b.256, I.b.268, I.b.271 and I.b.273, I.b.68, I.b.123, I.c.148, I.b.151, I.b.166, I.b.168, I.b.183, I.b.203, I.b.283, I.b.288, I.b.293, and I.c.298 at 200 ppm in the formulation give at least 80% disease control in this test when compared to untreated control leaf disks under the same conditions, which show extensive disease development.

*Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5 to 7 days after application).

Compounds I.b.268. I.b.273, I.b.168 and I.b.298 at 200 ppm in the formulation gives at least 80% disease control in this test when compared to untreated control leaf disks under the same conditions, which show extensive disease development.

*Monocraphella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.b.31, I.b.66, I.b.128, I.b.133, I.b.178, I.b.188, I.b.193, I.b.231, I.b.236, I.b.241, I.b.246, I.b.251, I.b.256, I.b.268, I.b.271, I.b.273, I.b.68, I.b.73, I.b.78, I.b.123, I.c.148, I.b.151, I.b.166, I.b.168, I.b.183, I.b.201, I.b.203, I.b.283, I.b.288, I.b.293, I.b.298 and I.c.298 at 200 ppm in the formulation give at least 80% disease control in this test when compared to untreated control leaf disks under the same conditions, which show extensive disease development.

*Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.b.31, I.b.66, I.b.128, I.b.133, I.b.178, I.b.193, I.b.231, I.b.251, I.b.256, I.b.268, I.b.271, I.b.273, I.b.123, I.c.148, I.b.151, I.b.166, I.b.168, I.b.183, I.b.201, I.b.203, I.b.283, I.b.293, I.b.298 and I.c.298 at 200 ppm in the formulation give at least 80% disease control in this test when compared to untreated control leaf disks under the same conditions, which show extensive disease development.

*Mycosphaerella graminicola* (*Septoria tritici*)/Liquid Culture (Septoria Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4 to 5 days after application.

Compounds I.b.31, I.b.66, I.b.128, I.b.133, I.b.178, I.b.188, I.b.193, I.b.231, I.b.236, I.b.246, I.b.251, I.b.256, I.b.268, I.b.271, I.b.273, I.b.33, I.b.68, I.b.78, I.b.123, I.c.148, I.b.151, I.b.166, I.b.168, I.b.183, I.b.201, I.b.203, I.b.283, I.b.288, I.b.293, I.b.298 and I.c.298 at 200 ppm in the formulation give at least 80% disease control in this test when compared to untreated control leaf disks under the same conditions, which show extensive disease development.

*Pyrenophora teres*/Barley/Leaf Disc Preventative (Net Blotch)

Barley leaf segments cv. Hasso are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 20° C. and 65% rh under a light regime of 12 h light/12 h darkness in a climate cabinet and the activity of a compound is assessed as disease control compared to untreated when an appropriate level of disease damage appears in untreated check leaf segments (5 to 7 days after application).

Compounds I.b.133, I.b.268, I.b.273, I.b.168, I.c.273 and I.c.298 at 200 ppm of the formulation give at least 80% disease control in this test when compared to untreated control leaf disks under the same conditions, which show extensive disease development.

*Thanatephorus cucumeris* (*Rhizoctonia solani*)/Liquid Culture (Foot Rot, Damping-off)

Mycelia fragments of a newly grown liquid culture of the fungus are directly mixed into nutrient broth (PDB potato dextrose broth). After placing a (DMSO) solution of the test compound into a microtiter plate (96-well format), the nutrient broth containing the fungal material is added. The test plates are incubated at 24° C. and the inhibition of growth is determined photometrically 3 to 4 days after application.

Compounds I.b.128, I.b.193 and I.b.168 at 200 ppm in the formulation give at least 80% disease control in this test when compared to untreated control leaf disks under the same conditions, which show extensive disease development.

The invention claimed is:
1. A compound of formula (I):

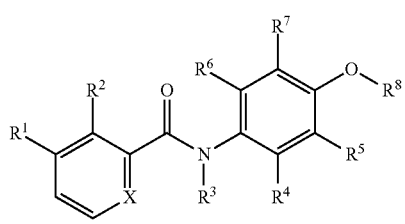

wherein,
$R^1$ is $C_1$-$C_6$alkoxy or $C_1$-$C_6$acylamino, wherein $C_1$-$C_6$alkoxy and $C_1$-$C_6$acylamino are optionally substituted with 1 to 3 groups represented by $R^9$; and
$R^2$ is hydroxyl, $C_1$-$C_6$acyloxy, $C_1$-$C_6$alkoxy$C_1$-$C_6$alkoxy or $C_1$-$C_6$acyloxy$C_1$-$C_6$alkoxy, wherein $C_1$-$C_6$acyloxy, $C_1$-$C_6$alkoxy$C_1$-$C_6$alkoxy and $C_1$-$C_6$acyloxy$C_1$-$C_6$alkoxy are optionally substituted with 1 to 3 groups represented by $R^9$; or
$R^1$ and $R^2$ together with the carbon atoms to which they are attached form a 1,3-oxazole ring;
$R^3$ is hydrogen, $C_1$-$C_6$alkyl, $C_1$-$C_6$alkoxy or $C_3$-$C_6$cycloalkyl;
$R^4$, $R^5$, $R^6$ and $R^7$ are independently hydrogen, halogen, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^9$;
$R^8$ is $C_7$-$C_9$cycloalkyl optionally substituted with 1 to 5 groups represented by $R^{10}$, wherein $R^{10}$ is independently selected from hydroxyl, halogen, cyano, $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy, wherein $C_1$-$C_6$alkyl, $C_1$-$C_6$alkoxy, $C_1$-$C_6$alkylthio, $C_1$-$C_6$alkylsulfonyl, $C_2$-$C_6$alkenyl, $C_2$-$C_6$alkynyl or $C_1$-$C_6$alkylcarbonyloxy are optionally substituted with 1 to 3 groups represented by $R^9$; or
$R^8$ is $C_3$-$C_9$cycloalkyl optionally substituted with 1 or 2 groups represented by $R^{10}$, wherein $R^{10}$ is independently selected from $C_3$-$C_6$cycloalkyl, aryl, heteroaryl, aryloxy, heteroaryloxy, aryl$C_1$-$C_6$alkyl, heteroaryl$C_1$-$C_6$alkyl, =O, =C($R^{11}$)$_2$, =NOR$^{11}$ or =N—N($R^{11}$)$_2$, wherein $C_3$-$C_6$cycloalkyl, aryl, heteroaryl, aryloxy, heteroaryloxy, aryl$C_1$-$C_6$alkyl or heteroaryl$C_1$-$C_6$alkyl are optionally substituted with 1 to 3 groups represented by $R^9$; or
$R^8$ is $C_3$-$C_9$cycloalkyl optionally substituted with 1 group represented by $R^{10}$, wherein $R^{10}$ is a spiro-annulated 3- to 10-membered saturated or partially unsaturated carbocyclic ring system or heterocyclic ring system containing 1 or 2 heteroatoms selected from oxygen, nitrogen and sulfur, and optionally substituted by 1 to 3 groups represented by halogen, $C_1$-$C_4$alkyl or =O;
$R^9$ is independently selected from halogen, cyano, $C_1$-$C_4$alkyl and $C_1$-$C_4$alkoxy, wherein $C_1$-$C_4$alkyl and $C_1$-$C_4$alkoxy are optionally substituted by 1 to 5 groups represented by halogen;
$R^{11}$ is hydrogen, $C_1$-$C_6$alkyl, $C_2$-$C_6$alkenyl, $C_2$-$C_6$alkynyl or aryl, wherein $C_1$-$C_6$alkyl, $C_2$-$C_6$alkenyl, $C_2$-$C_6$alkynyl and aryl are optionally substituted with 1 to 3 groups represented by $R^9$; and
X is CH or N;
or a salt or an N-oxide thereof.

2. The compound according to claim 1, wherein $R^1$ is $C_1$-$C_4$alkoxy and $R^2$ is hydroxyl.

3. The compound according to claim 1, wherein $R^3$ is hydrogen.

4. The compound according to claim 1, wherein $R^4$ is selected from halogen, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^9$.

5. The compound according to claim 1, wherein $R^4$ is hydrogen, fluorine or chlorine and $R^5$, $R^6$ and $R^7$ are hydrogen.

6. The compound according to claim 1, wherein $R^8$ is $C_5$-$C_8$cycloalkyl optionally substituted with 1 or 2 groups represented by $R^{10}$, wherein $R^{10}$ is independently selected from $C_3$-$C_6$cycloalkyl, aryl, =C($R^{11}$)$_2$, =NOR$^{11}$ or spiro-annulated 1,3-dioxolan-2-yl, wherein $C_3$-$C_6$cycloalkyl, aryl, =C($R^{11}$)$_2$ and =NOR$^{11}$ are optionally substituted with 1 to 3 groups represented by $R^9$, or wherein spiro-annulated 1,3-dioxolan-2-yl is optionally substituted with 1 to 3 groups represented by halogen, $C_1$-$C_4$alkyl or =O; or $R^8$ is $C_7$-$C_8$cycloalkyl optionally substituted with 1 or 2 groups represented by $R^{10}$, wherein $R^{10}$ is independently selected from hydroxyl, $C_1$-$C_6$alkyl, or $C_1$-$C_6$alkylcarbonyloxy, wherein $C_1$-$C_6$alkyl is optionally substituted with 1 to 3 groups represented by $R^9$; and $R^{11}$ is independently selected from hydrogen, $C_1$-$C_6$alkyl, $C_2$-$C_6$alkenyl, $C_2$-$C_6$alkynyl and aryl.

7. The compound according to claim 6, wherein $R^8$ is $C_5$-$C_8$cycloalkyl optionally substituted with 1 or 2 groups represented by $R^{10}$, wherein $R^{10}$ is independently selected from $C_6$cycloalkyl, phenyl, $=C(R^{11})_2$ or $=NOR^{11}$, or $R^8$ is $C_7$-$C_8$cycloalkyl optionally substituted with 1 or 2 groups represented by $R^{10}$, wherein $R^{10}$ is independently selected from hydroxyl, $C_1$-$C_4$alkyl, or $C_1$-$C_6$alkylcarbonyloxy; and $R^{11}$ is independently selected from hydrogen, $C_1$-$C_4$alkyl, $C_2$-$C_4$alkenyl, $C_2$-$C_4$alkynyl and phenyl.

8. The compound according to claim 1, wherein X is N.

9. The compound according to claim 1, selected from any one of:

N-[4-(cycloheptoxy)phenyl]-3-hydroxy-4-methoxy-pyridine-2-carboxamide;

N-[4-(cycloheptoxy)-2-fluoro-phenyl]-3-hydroxy-4-methoxy-pyridine-2-carboxamide;

N-[4-(cyclooctoxy)phenyl]-3-hydroxy-4-methoxy-pyridine-2-carboxamide; or

N-[4-(cyclooctoxy)-2-fluoro-phenyl]-3-hydroxy-4-methoxy-pyridine-2-carboxamide.

10. An agrochemical composition comprising a fungicidally effective amount of a compound of formula (I) according to claim 1.

11. The composition according to claim 10, further comprising at least one additional active ingredient and/or an agrochemically-acceptable diluent or carrier.

12. A method of controlling or preventing infestation of useful plants by phytopathogenic microorganisms, wherein a fungicidally effective amount of a compound of formula (I) according to claim 1, or a composition comprising this compound as active ingredient, is applied to the plants, to parts thereof or the locus thereof.

* * * * *